US009512130B2

(12) United States Patent
Koppitz et al.

(10) Patent No.: US 9,512,130 B2
(45) Date of Patent: Dec. 6, 2016

(54) SUBSTITUTED IMIDAZOPYRIDAZINES

(71) Applicant: BAYER PHARMA AKTIENGESELLSCHAFT, Berlin (DE)

(72) Inventors: Marcus Koppitz, Berlin (DE); Ulrich Klar, Berlin (DE); Antje Margret Wengner, Berlin (DE); Roland Neuhaus, Berlin (DE); Gerhard Siemeister, Berlin (DE); Michael Brüning, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/771,648

(22) PCT Filed: Feb. 25, 2014

(86) PCT No.: PCT/EP2014/053573
§ 371 (c)(1),
(2) Date: Aug. 31, 2015

(87) PCT Pub. No.: WO2014/131739
PCT Pub. Date: Sep. 4, 2014

(65) Prior Publication Data

US 2016/0016959 A1 Jan. 21, 2016

(30) Foreign Application Priority Data

Mar. 1, 2013 (EP) .................................... 13157453
Dec. 20, 2013 (EP) .................................... 13198930

(51) Int. Cl.

| | |
|---|---|
| ***A61K 31/4188*** | (2006.01) |
| ***C07D 237/00*** | (2006.01) |
| ***C07D 487/04*** | (2006.01) |
| ***A61K 31/282*** | (2006.01) |
| ***A61K 31/5025*** | (2006.01) |
| ***A61K 31/52*** | (2006.01) |
| ***A61K 31/573*** | (2006.01) |
| ***A61K 31/675*** | (2006.01) |
| ***A61K 31/69*** | (2006.01) |
| ***A61K 31/704*** | (2006.01) |
| ***A61K 31/7068*** | (2006.01) |
| ***A61K 33/24*** | (2006.01) |
| ***A61K 38/14*** | (2006.01) |
| ***A61K 39/395*** | (2006.01) |
| *A61K 39/00* | (2006.01) |

(52) U.S. Cl.
CPC ........... *C07D 487/04* (2013.01); *A61K 31/282* (2013.01); *A61K 31/4188* (2013.01); *A61K 31/5025* (2013.01); *A61K 31/52* (2013.01); *A61K 31/573* (2013.01); *A61K 31/675* (2013.01); *A61K 31/69* (2013.01); *A61K 31/704* (2013.01); *A61K 31/7068* (2013.01); *A61K 33/24* (2013.01); *A61K 38/14* (2013.01); *A61K 39/3955* (2013.01); *C07D 237/00* (2013.01); *A61K 2039/505* (2013.01)

(58) Field of Classification Search
CPC .................... A61K 31/5025; A61K 31/4188; C07D 237/00
USPC .......................................... 514/248; 544/236
See application file for complete search history.

(56) References Cited

FOREIGN PATENT DOCUMENTS

WO WO 2010042699 A1 * 4/2010 .......... C07D 487/04

* cited by examiner

*Primary Examiner* — Kamal Saeed
*Assistant Examiner* — Janet L Coppins

(57) ABSTRACT

The present invention relates to substituted imidazopyridazine compounds, to methods of preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

10 Claims, No Drawings

SUBSTITUTED IMIDAZOPYRIDAZINES

The present invention relates to substituted imidazopyridazine compounds as described and defined herein, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, TTK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mot Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumourigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81]. Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Established anti-mitotic drugs such as vinca alkaloids, taxanes or epothilones activate the SAC inducing a mitotic arrest either by stabilising or destabilising microtubule dynamics. This arrest prevents separation of sister chromatids to form the two daughter cells. Prolonged arrest in mitosis forces a cell either into mitotic exit without cytokinesis or into mitotic catastrophe leading to cell death.

In contrast, inhibitors of Mps-1 induce a SAC inactivation that accelerates progression of cells through mitosis resulting in severe chromosomal missegregation and finally in cell death.

These findings suggest that Mps-1 inhibitors should be of therapeutic value for the treatment of proliferative disorders associated with enhanced uncontrolled proliferative cellular processes such as, for example, cancer, inflammation, arthritis, viral diseases, neurodegenerative diseases such as Alzheimer's disease, cardiovascular diseases, or fungal diseases in a warm-blooded animal such as man. Therefore, inhibitors of Mps-1 represent valuable compounds that should complement therapeutic options either as single agents or in combination with other drugs.

Different compounds have been disclosed in prior art which show an inhibitory effect on Mps-1 kinase. WO2010/124826A1 discloses substituted imidazoquinoxaline compounds as inhibitors of Mps-1 kinase. WO2011/026579A1 discloses substituted aminoquinoxalines as Mps-1 inhibitors. WO2011/063908A1, WO2011/064328A1 as well as WO2011/063907 A1 disclose triazolopyridine derivates as inhibitors of Mps-1 kinase.

Imidazopyridazine derivates have been disclosed for the treatment or prophylaxis of different diseases:

WO 2007/038314 A2 relates to fused heterocyclic compounds useful as kinase modulators, including MK2 modulation. In particular, WO 2007/038314 A2 relates to imidazo[1,2-b]pyridazines.

US patent application publication US 2008/0045536 A1 similarly relates to fused heterocyclic compounds useful as kinase modulators, including MK2 modulation. In particular, it relates to imidazo[1,2-b]pyridazines.

WO 2010/042699 A1 relates to fused heterocyclic compounds useful as kinase modulators, particularly CK2 modulation. In particular, WO 2010/042699 A1 relates to imidazo[1,2-b]pyridazines which are substituted with a nitrite group in position 3.

WO 2007/025090 A2 relates to heterocyclic compounds useful as inhibitors of MEK kinase. In particular, WO 2007/025090 A2 relates inter alia to imidazo[1,2-b]pyridazines.

WO 1998/08847 A1 relates to heterocyclic compounds useful as corticotropin releasing factor (hormone) CRF (CRH) antagonists. In particular, WO 1998/08847 A1 relates inter alia to imidazo[1,2-b]pyridazines.

WO 2011/013729A1 discloses fused imidazole derivatives as Mps-1 inhibitors. Among the disclosed fused imidazole derivates there are also imidazo[1,2-b]pyridazines.

WO 2012/032031A1 inter alia is related to imidazo[1,2-b]pyridazines as Mps-1 inhibitors.

However, the state of the art described above does not specifically describe the imidazopyridazine compounds of formula (A), (B) or (C), or a stereoisomer, a tautomer, an N-oxide, a hydrate, a solvate, or a salt thereof, or a mixture of same, as described and defined herein, and as hereinafter referred to as "compounds of the present invention", or their pharmacological activity and stability.

It has now been found, and this constitutes the basis of the present invention, that said compounds of the present invention have surprising and advantageous properties.

In particular, said compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The compounds of the present invention surprisingly exhibit a superior overall profile with respect to Mps-1-related activity in a functional assay (Spindle Assembly Checkpoint Assay), antiproliferative activity (Proliferation Assay with HeLa cells), metabolic stability (in vitro metabolic stability in rat hepatocytes) and drug-drug interaction potential (inhibition of liver enzyme CYP3A4), as will be shown hereinafter.

SUMMARY OF THE INVENTION

The present invention covers compounds of formulae (A), (B), and (C):

(A)

-continued

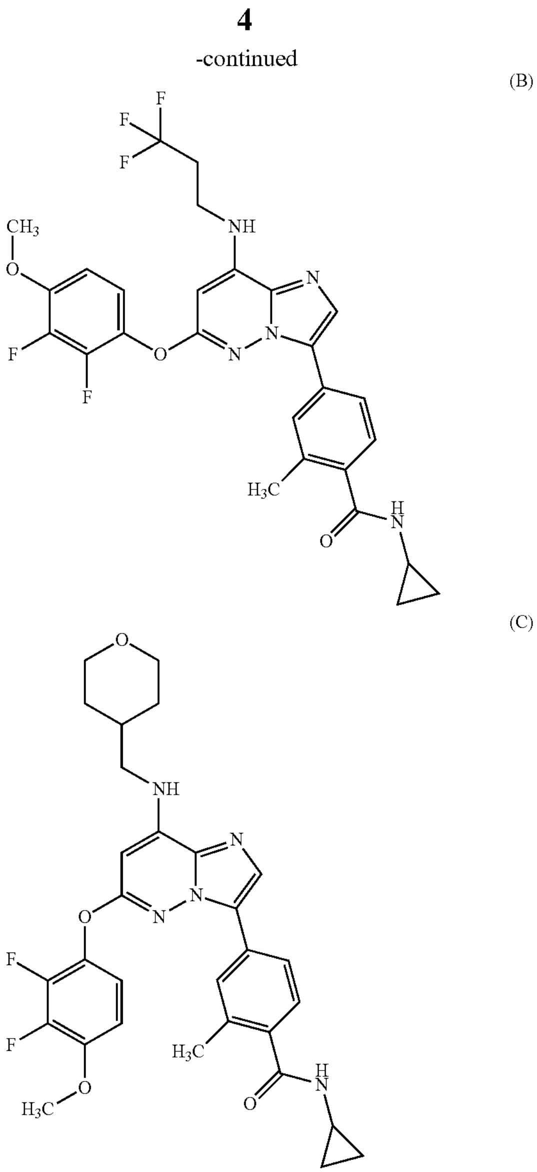

or a stereoisomer, a tautomer, an N-oxide, a hydrate, a solvate, or a salt thereof, or a mixture of same.

The compounds of the present invention are characterized by: activity in Spindle Assembly Checkpoint Assay $<1.0$ nM, activity in Proliferation Assay with HeLa cells $<25$ nM, in vitro metabolic stability in rat hepatocytes Fmax $\geq 39\%$, and inhibition of liver enzyme CYP3A4 $\geq 5$ μM.

The present invention also relates to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "$C_1$-$C_6$", as used throughout this text, e.g. in the context of the definition of "$C_1$-$C_6$-alkyl", is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

As used herein, the term "Leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

In accordance with a first aspect, the present invention is directed to a compound of formula (A), (B) or (C):

(A)

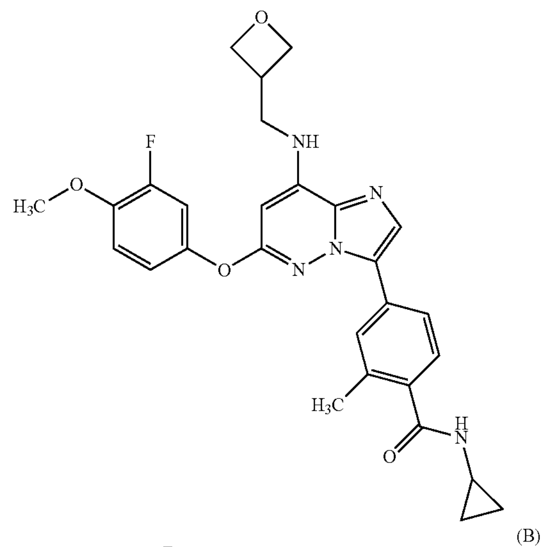

(B)

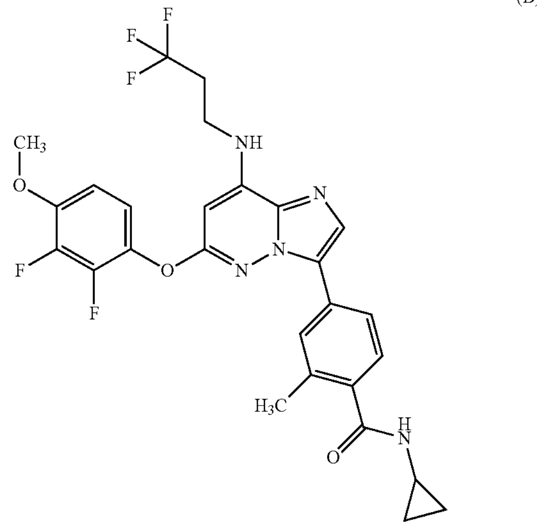

(C)

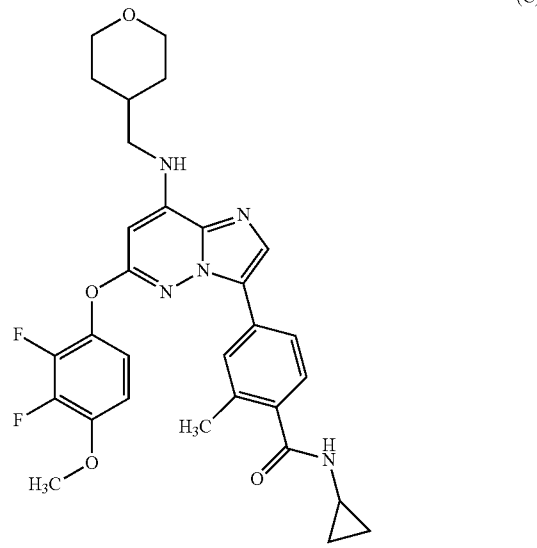

In a preferred embodiment, the invention relates to a compound of formula (A), supra.

In another preferred embodiment, the invention relates to a compound of formula (B), supra.

In another preferred embodiment, the invention relates to a compound of formula (C), supra.

In an embodiment of the above-mentioned aspect, the invention relates to a compound of formulae (A), (B) or (C) in the form of a tautomer, an N-oxide, a hydrate, a solvate, or a salt thereof, or a mixture of same.

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

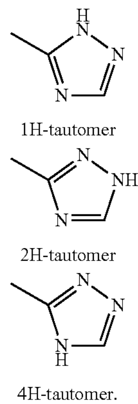

The present invention includes all possible tautomers of the compounds of the present invention as single tautomers, or as any mixture of said tautomers, in any ratio.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}H$ (deuterium), $^{3}H$ (tritium), $^{11}C$ $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Further, the compounds of the present invention can exist as N-oxides, which are defined in that at least one nitrogen of the compounds of the present invention is oxidised. The present invention includes all such possible N-oxides.

Furthermore, the present invention includes all possible crystalline forms, or polymorphs, of the compounds of the present invention, either as single polymorphs, or as a mixture of more than one polymorph, in any ratio.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

The present invention also relates to useful forms of the compounds as disclosed herein, such as metabolites, hydrates, solvates, prodrugs, salts, in particular pharmaceutically acceptable salts, in vivo hydrolysable esters, and co-precipitates. The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, Lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, Lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol.

Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

The compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Therefore, the compounds of formulae (A), (B), and (C), supra, are expected to be valuable as therapeutic agents.

Accordingly, in another embodiment, the present invention is directed to a compound of formula (A), (B) or (C), supra, or a stereoisomer, a tautomer, an N-oxide, a hydrate, a solvate, or a salt thereof, particularly a pharmaceutically acceptable salt thereof, or a mixture of same, for use in the treatment or prophylaxis of a disease.

In another embodiment, the present invention provides a method of treating disorders associated with enhanced uncontrolled proliferative cellular processes in a patient in need of such treatment, comprising administering to the patient an effective amount of a compound of formula (A), (B) or (C), supra.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The terms "cell proliferative disorder" or "disorder associated with enhanced uncontrolled proliferative cellular processes" include disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

In another embodiment, the present invention is directed to a compound of formula (A), (B) or (C), or a stereoisomer, a tautomer, an N-oxide, a hydrate, a solvate, or a salt thereof, particularly a pharmaceutically acceptable salt thereof, or a mixture of same, for use in the treatment or prophylaxis of a disease, wherein said disease is a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is mediated by the mitogen-activated protein kinase (MEK-ERK) pathway, more particularly in which the disease of uncontrolled cell growth, proliferation and/or survival, inappropriate cellular immune response, or inappropriate cellular inflammatory response is a haemotological tumour, a solid tumour and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Compounds of formulae (A), (B), and (C), supra, may be administered as the sole pharmaceutical agent or in combination with one or more additional therapeutic agents where the combination causes no unacceptable adverse effects. This combination therapy includes administration of a single pharmaceutical dosage formulation which contains a compound of formula (A), (B) or (C) and one or more additional therapeutic agents, as well as administration of the compound of formula (A), (B) or (C) and each additional therapeutic agent in its own separate pharmaceutical dosage formulation. For example, a compound of formula (A), (B) or (C) and a therapeutic agent may be administered to the patient together in a single oral dosage composition such as a tablet or capsule, or each agent may be administered in separate dosage formulations.

Where separate dosage formulations are used, the compound of formula (A), (B) or (C) and one or more additional therapeutic agents may be administered at essentially the same time (e.g., concurrently) or at separately staggered times (e.g., sequentially).

In another aspect, the invention provides a pharmaceutical composition comprising a compound of general formula (A), (B) or (C), or a stereoisomer, a tautomer, an N-oxide, a hydrate, a solvate, or a salt thereof, particularly a pharmaceutically acceptable salt thereof, or a mixture of same, and a pharmaceutically acceptable diluent or carrier.

Preferably, the pharmaceutical combination comprises:

- one or more compounds of general formula (A), (B) or (C), or a stereoisomer, a tautomer, an N-oxide, a hydrate, a solvate, or a salt thereof, particularly a pharmaceutically acceptable salt thereof, or a mixture of same; and
- one or more agents selected from: a taxane, such as Docetaxel, Paclitaxel, or Taxol; an epothilone, such as Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2-deoxyadenosine; Thioguanine; an anti-androgen, such as Flutamide, Cyproterone acetate, or Bicalutamide; Bortezomib; a platinum derivative, such as Cisplatin, or Carboplatin; Chlorambucil; Methotrexate; and Rituximab.

In still another aspect, the invention provides a process for preparing a pharmaceutical composition. The process includes the step of combining at least one compound of formula (A), (B) or (C) as defined above with at least one pharmaceutically acceptable carrier, and bringing the resulting combination into a suitable administration form.

In still another aspect, the invention provides use of a compound of formula (A), (B) or (C) as defined above for manufacturing a pharmaceutical composition for the treatment or prevention of a cell proliferative disorder. In certain embodiments, the cell proliferative disorder is cancer.

The active component of formula (A), (B) or (C) can act systemically and/or locally. For this purpose, it can be applied in a suitable manner, for example orally, parenterally, pulmonally, nasally, sublingually, lingually, buccally, rectally, transdermally, conjunctivally, optically, or as an implant or stent.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Regardless of the route of administration selected, the compounds of the invention, which may be used in a suitable hydrated form, and/or the pharmaceutical compositions of the present invention, are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient.

In accordance with another aspect, the present invention covers methods of preparing compounds of the present invention.

In accordance with a first embodiment, the present invention also relates to a method of preparing a compound of formula (A), (B) or (C), supra, said method comprising the step of allowing an intermediate compound of general formula (A1), (B1) or (C1):

(A1)

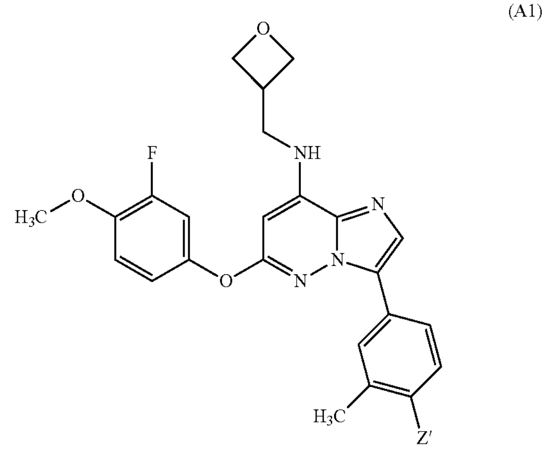

(B1)

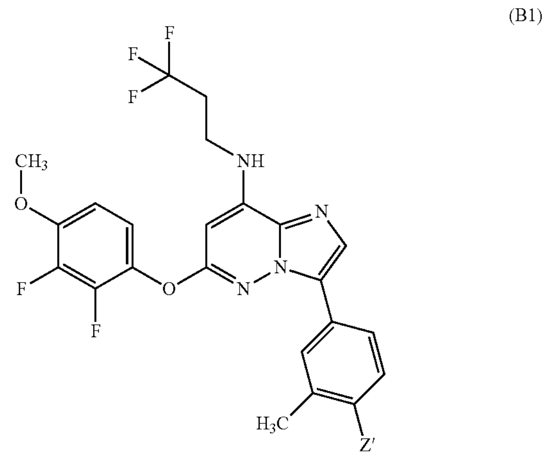

-continued (C1)

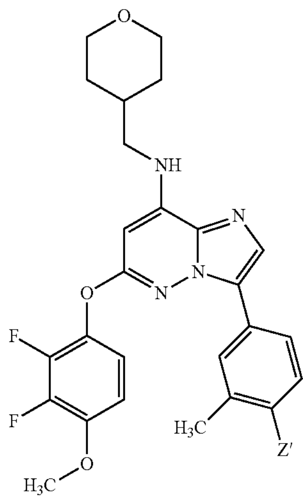

in which Z' represents a group selected from: —C(═O)OH and —C(═O)O—($C_1$-$C_6$-alkyl); to react with a compound of formula Ib:

Ib

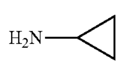

thereby giving, upon optional deprotection, a compound of formula (A), (B) or (C).

In accordance with another embodiment, the present invention also relates to a method of preparing a compound of formula (A), (B) or (C), supra, said method comprising the step of allowing an intermediate compound of formula (A2), (B2) or (C2):

(A2)

(B2)

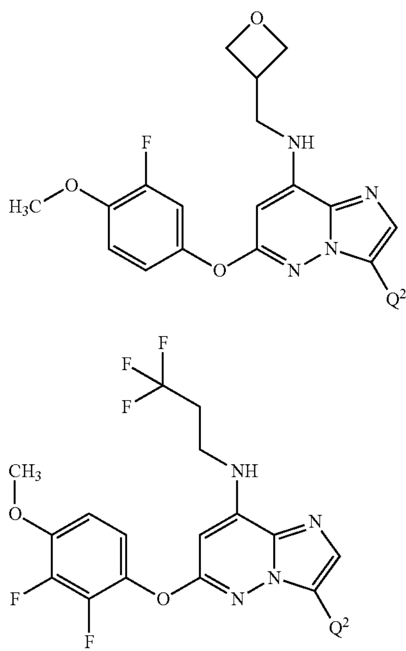

-continued (C2)

in which $Q^2$ is a leaving group, preferably $Q^2$ is a halogen atom;

to react with a compound of general formula IIa:

IIa in which Y is a substituent which is displaced in a coupling reaction, such as a boronic acid group, or an ester of a boronic acid group, for example; thereby giving, upon optional deprotection, a compound of formula (A), (B) or (C).

In accordance with another embodiment, the present invention also relates to a method of preparing a compound of formula (A), (B) or (C), supra, said method comprising the step of allowing an intermediate compound of formula (A3), (B3) or (C3):

(A3)

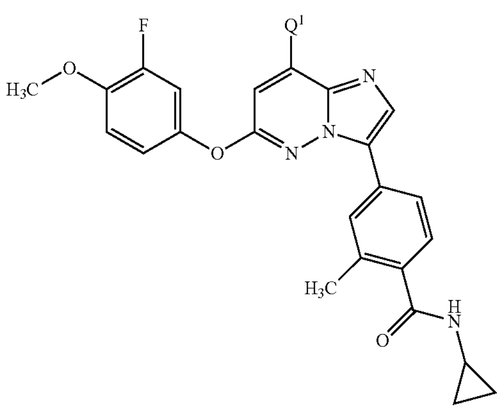

-continued
(B3)
(C3)
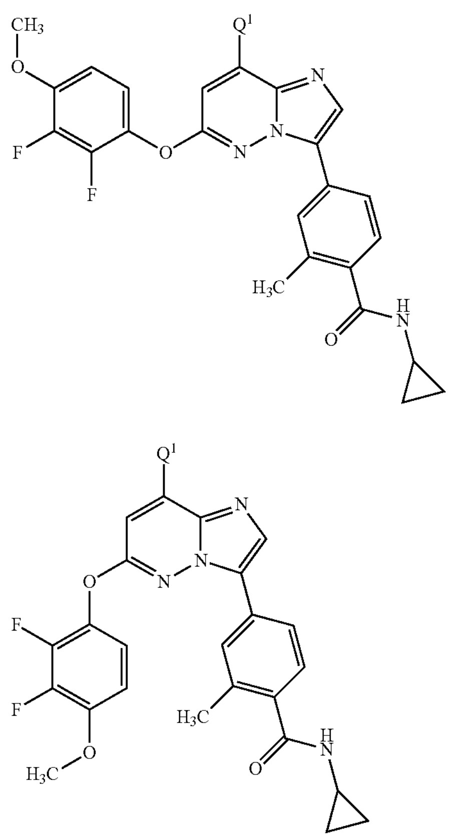
in which $Q^1$ is a leaving group, for example a halogen atom; to react with a compound of general formula (A4), (B4) or (C4):
(A4)
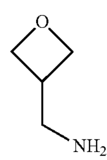
(B4)
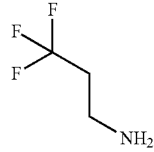
(C4)
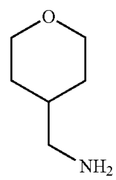
thereby giving, upon optional deprotection, a compound of general formula (A), (B) or (C):
(A)
(B)
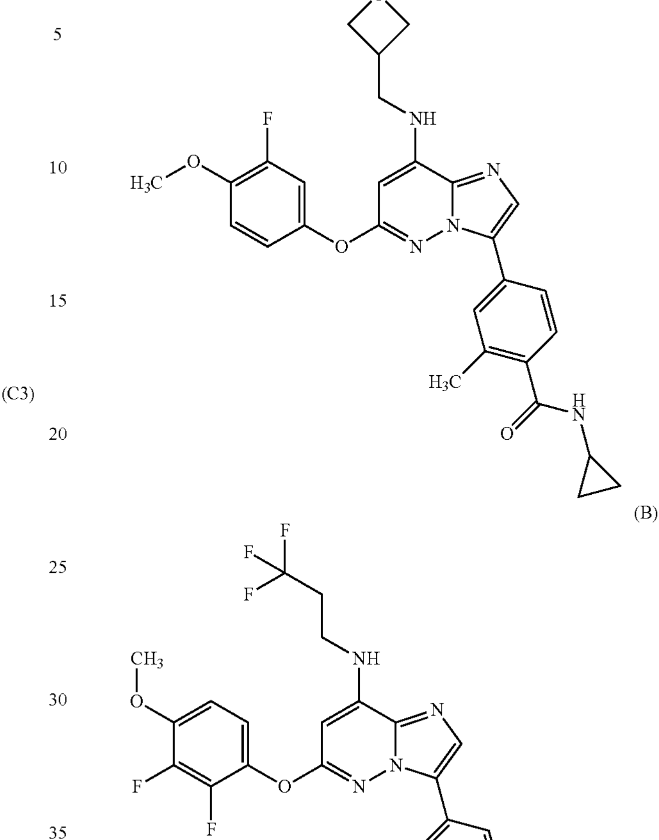
(C)
In accordance with another embodiment, the present invention also relates to a method of preparing a compound of formula (A), (B) or (C), supra, said method comprising the step of allowing an intermediate compound of formula (A5), (B5) or (C5):
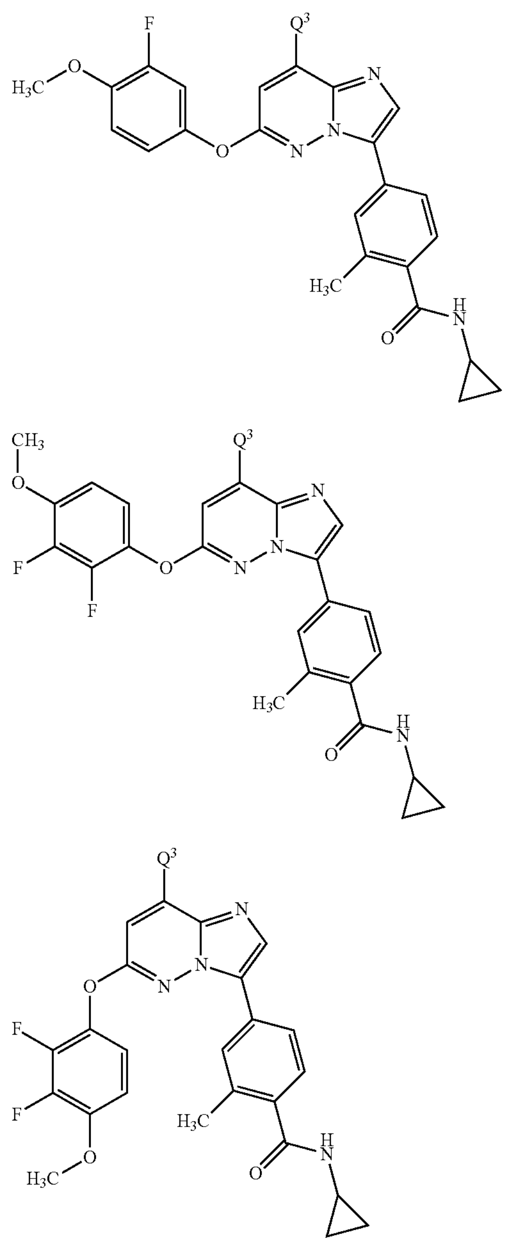
in which $Q^3$ is an optionally protected $NH_2$-group; to react with a compound of general formula (A6), (B6) or (C6):
(A6)
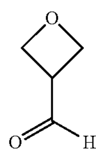
-continued
(B6)
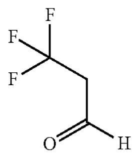
(C6)
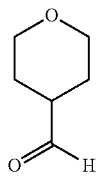
thereby giving, after reduction of the imine, and upon optional deprotection, a compound of formula (A), (B) or (C):
(A)
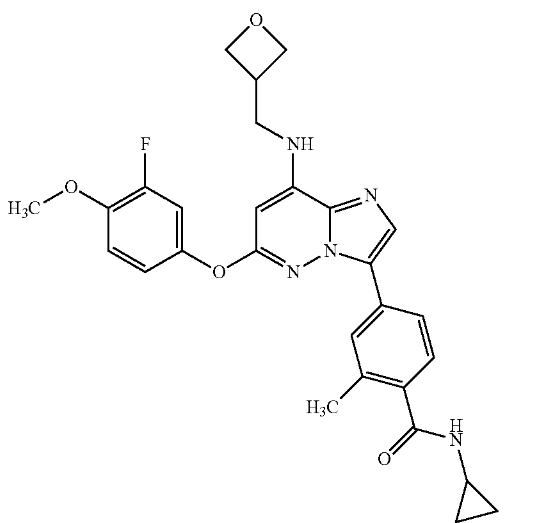
(B)
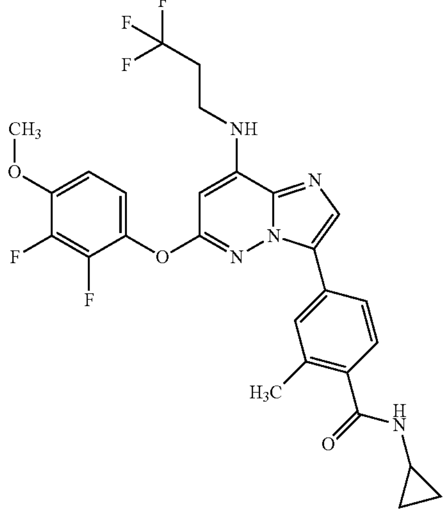

-continued (C)

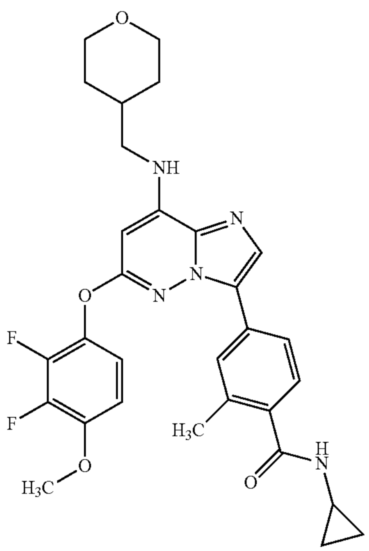

In accordance with another embodiment, the present invention relates to a method of preparing a compound of formula (A), (B) or (C), said method comprising the step of allowing an intermediate compound of formula (A7), (B7) or (C7):

(A7)

-continued (B7)

(C7)

in which $R^{3'}$ is a leaving group;

to react with a compound of formula (A8), (B8) or (C8):

(A8)

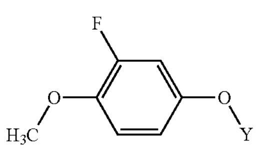

(B8)

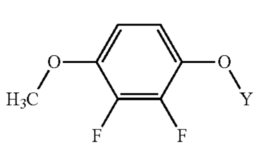

(C8)

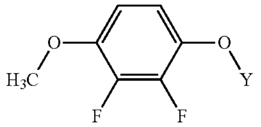

in which Y is a substituent which is displaced in a coupling reaction, such as a hydrogen atom, or a boronic acid group, or a boronic ester group, for example;

thereby giving a compound of formula (A), (B) or (C):

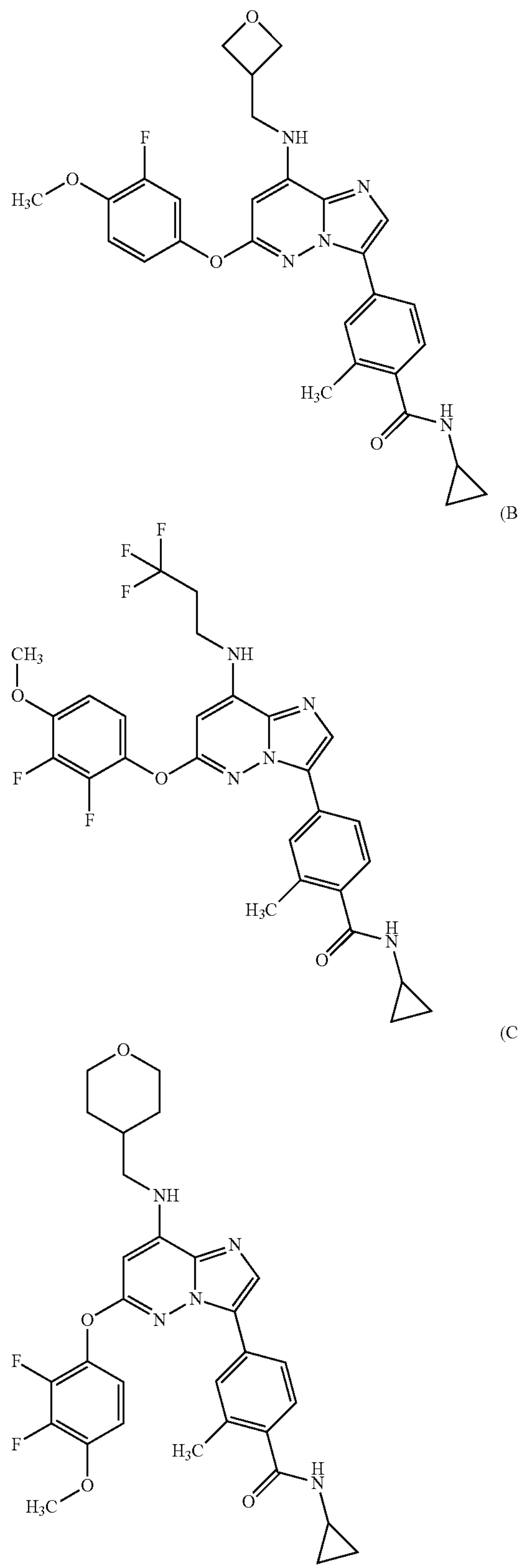

In accordance with a further aspect, the present invention covers intermediate compounds which are useful in the preparation of compounds of the present invention of formula (A), (B) or (C), particularly in the method described herein.

In particular, the present invention covers intermediate compounds of formula (A1), (B1) and (C1):

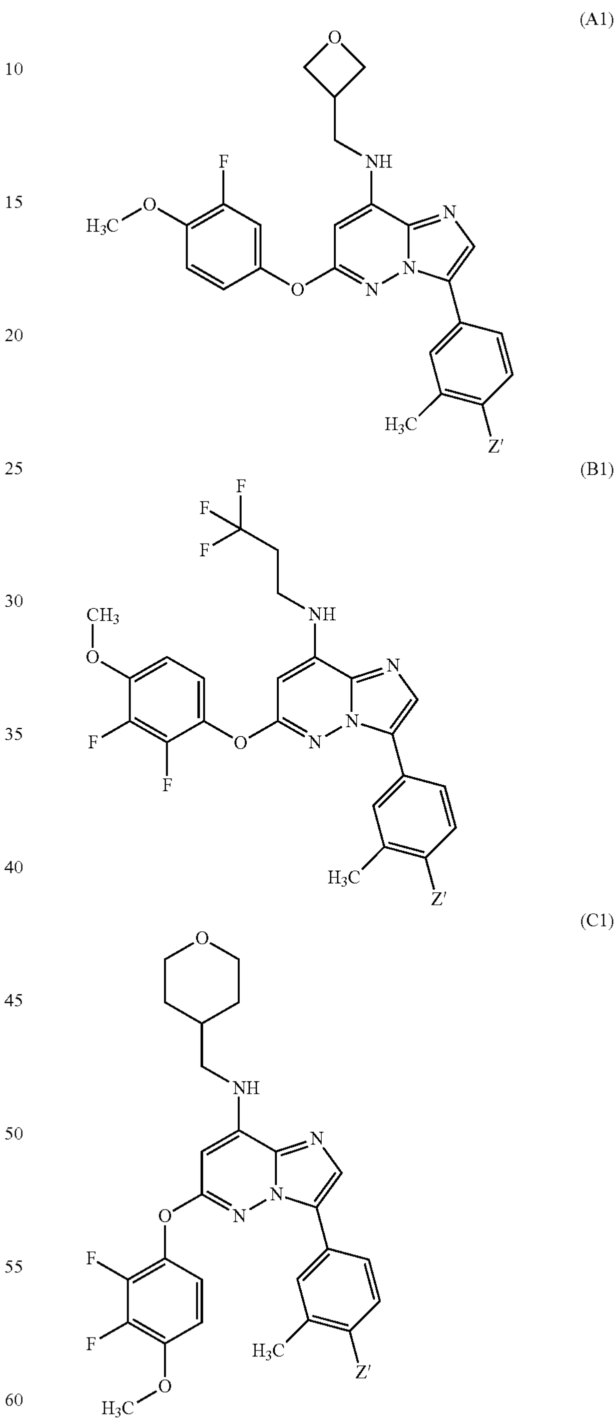

in which Z' represents a group selected from: —C(═O)OH and —C(═O)O—($C_1$-$C_6$-alkyl).

In accordance with yet another aspect, the present invention covers intermediate compounds of formula (A2), (B2) or (C2):

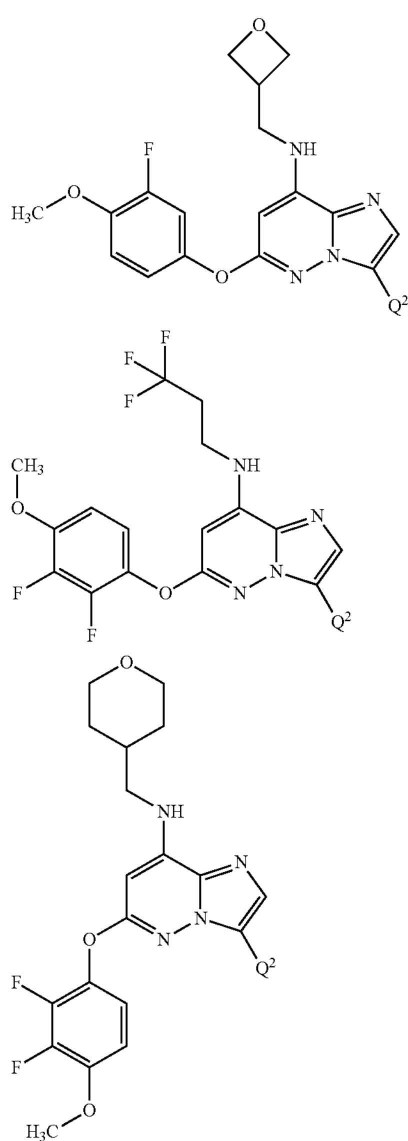
in $Q^2$ is a leaving group, preferably $Q^2$ is a halogen atom.
In accordance with a further aspect, the present invention covers intermediate compounds of formula (A3), (B3) or (C3):
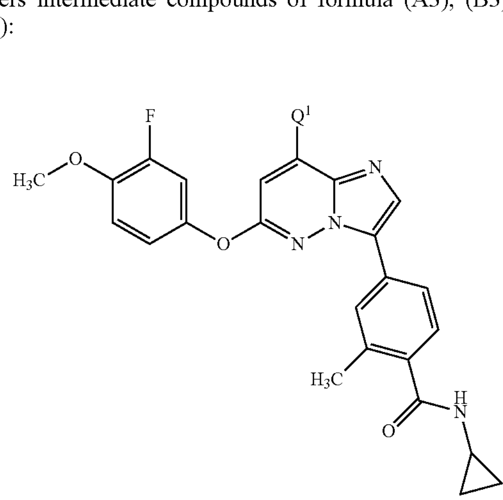
-continued
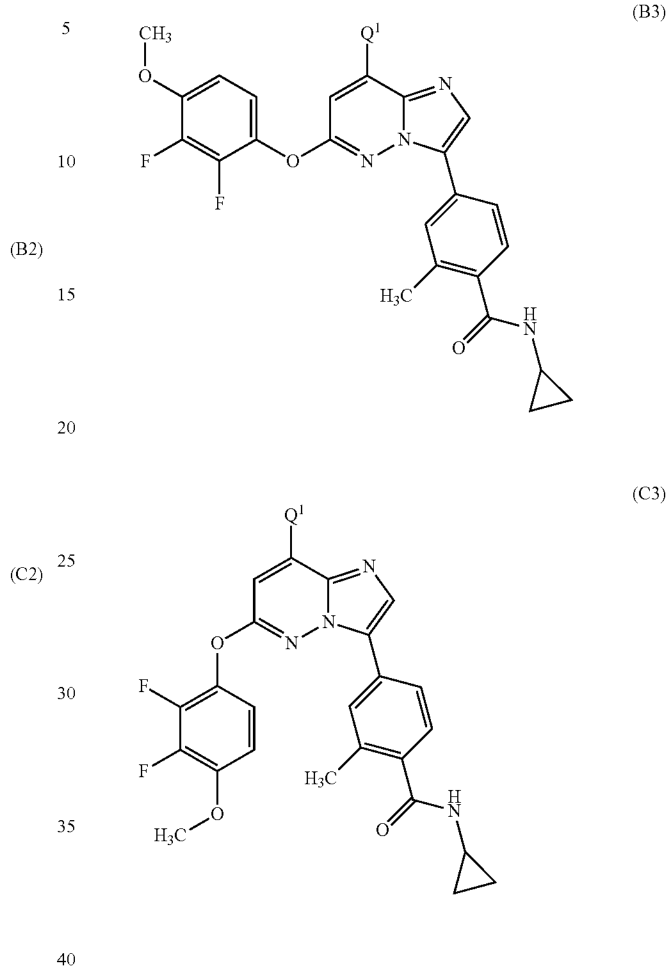
in which $Q^1$ is a leaving group, for example a halogen atom.
In accordance with a further aspect, the present invention covers intermediate compounds of formula (A5), (B5) or (C5):
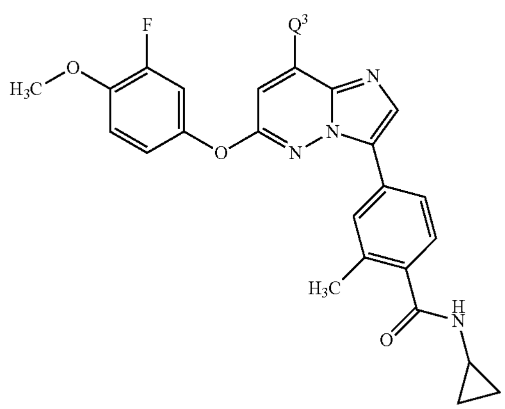

-continued (B5)

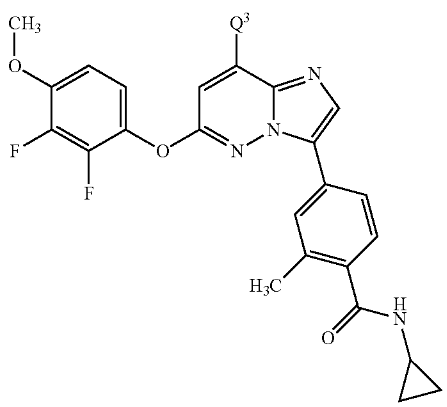

(C5)

in which $Q^3$ is an optionally protected $NH_2$-group.

In accordance with a further aspect, the present invention covers intermediate compounds of general formula (A7), (B7) or (C7):

(A7)

-continued (B7)

(C7)

in which $R^{3'}$ is a leaving group.

In accordance with a further aspect, the present invention relates to the use of a compound of formula (A1), (A2), (A3), (A4), (A5), (A6), (A7) or (A8), supra, for the preparation of a compound of formula (A), supra.

In accordance with a further aspect, the present invention relates to the use of a compound of formula (B1), (B2), (B3), (B4), (B5), (B6), (B7) or (B8), supra, for the preparation of a compound of formula (B), supra.

In accordance with a further aspect, the present invention relates to the use of a compound of formula (C1), (C2), (C3), (C4), (C5), (C6), (C7) or (C8), supra, for the preparation of a compound of formula (C), supra.

EXPERIMENTAL SECTION

General

The following Table lists the abbreviations used in this paragraph, and in the Examples section.

sss

| Abbreviation | Meaning |
|---|---|
| EDC | 1-Ethyl-3-(3-dimethyllaminopropyl)carbodiimide |
| DIPEA | N,N-diisopropylethylamine |
| DMF | N,N-Dimethylformamide |
| DMSO | Dimethyl sulfoxide |
| DIPEA | Diisopropylethylamine |
| Pd(dppf)$Cl_2$ | Dichloro[1,1'-bis(diphenylphosphino)ferrocene]palladi-um(II) |
| NMR | Nuclear magnetic resonance spectroscopy |
| rt | Room temperature |
| RT | Retention time in minutes |
| MW | Molecular weight |
| NMP | N-methylpyrrolidinone |
| Oxone | Potassium peroxymonosulfate |
| UPLC | Ultra performance liquid chromatography |

Synthesis of the Compounds of the Present Invention

Compounds of formula (A), (B) or (C) can be synthesized as depicted in the Scheme, in which A represents

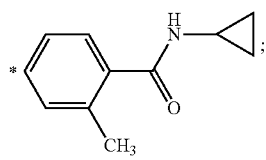

$R^3$ represents

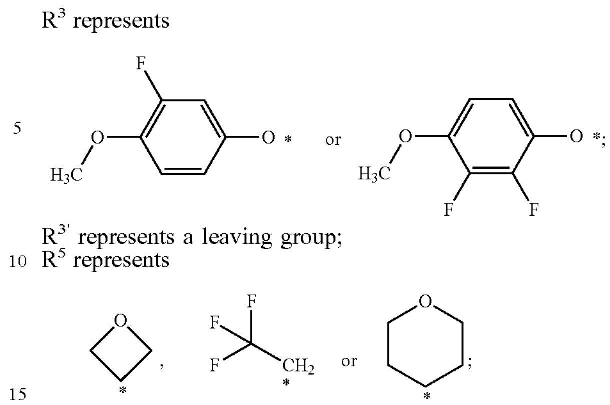

$R^{3'}$ represents a leaving group;

$R^5$ represents $Q^1$ represents a leaving group or an optionally protected $NH_2$-group; and $Q^2$ represents a leaving group;

wherein * indicates the point of attachment of said groups with the rest of the molecule.

Examples for typical leaving groups include but are not limited to halogen atoms like a chlorine, bromine or iodine atom, or a group selected from: methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

Scheme

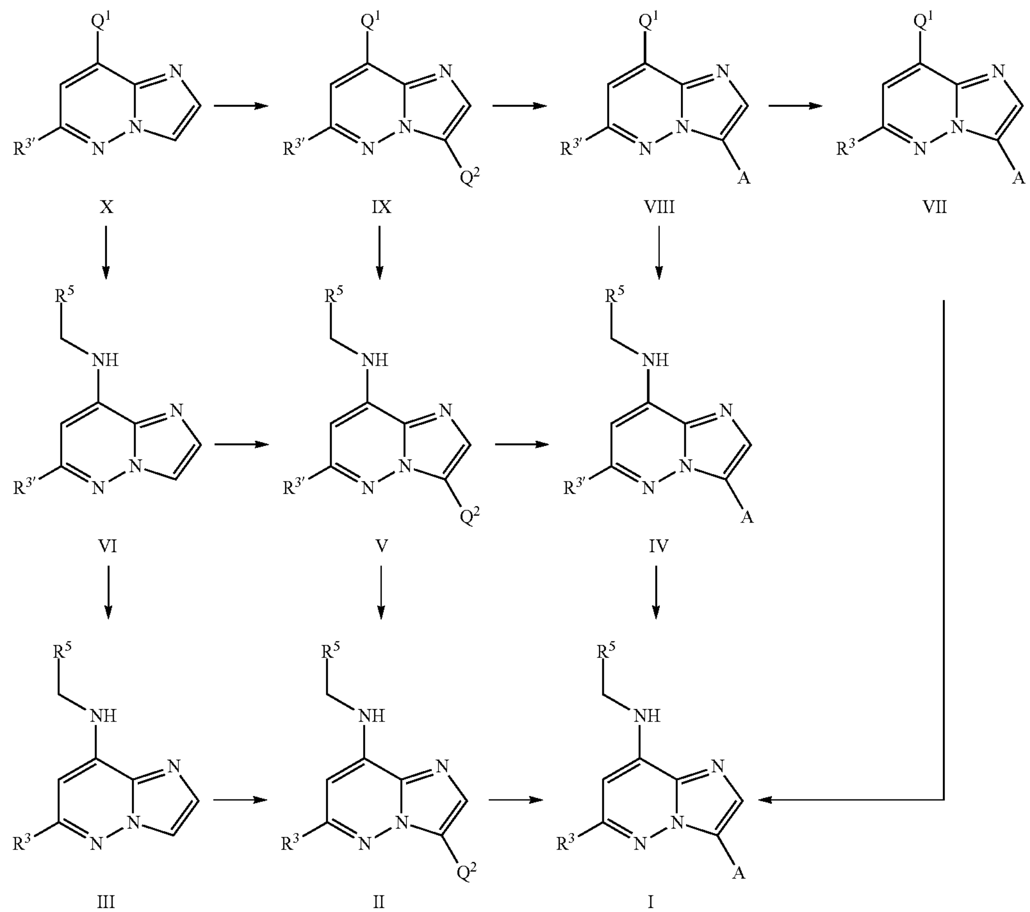

The Scheme exemplifies routes that allow variations for $R^3$, $R^{3'}$, $R^5$, $Q^1$, $Q^2$ and A during the synthesis. Functional moieties in $R^3$, $R^{3'}$, $R^5$, $Q^1$, $Q^2$ and A can be converted at every suitable stage of the synthesis.

Compounds of formula X may be commercially available or can be synthesized according to procedures known to persons skilled in the art, for example applying procedures described in WO2007/38314A2.

A leaving group $Q^2$ can be introduced in compounds of general formula X, VI or III by procedures known to persons skilled in the art to give compounds of general formula IX, V or II. As an example, halogens can be introduced using halogenation reagents like N-iodosuccinimide (NIS), N-bromosuccinimide (NBS), or N-chlorosuccinimide (NCS), in an inert solvent like N,N-dimethylformamide or 1-methylpyrrolidin-2-one, for example, at temperatures ranging from room temperature to the boiling point of the solvent, for example.

Compounds of general formula I, IV or VIII can be obtained from compounds of general formula II, V or IX via a coupling reaction between a reagent of formula Y-A, in which A is defined supra and Y represents a suitable functional group by which the group A can be transferred to the Q-group bearing carbon atom of compounds of formula II, V or IX. Examples of suitable functional groups for Y in A-Y include boronic acids $A\text{-}B(OH)_2$, or esters of boronic acids $A\text{-}B(OC_1\text{-}C_6\text{-alkyl})_2$. Said coupling reactions are performed in the presence of suitable catalysts, such as, for example, palladium based catalysts like, for example, Palladium (II) acetate, tetrakis(triphenylphosphine)palladium (0), bis(triphenylphosphine)-palladium (II) chloride or (1,1,-bis(diphenylphosphino) ferrocene)-dichloropalladium (II) and optionally suitable additives such as, for example, phosphines like, for example, $P(oTol)_3$ or triphenylphosphine and optionally with a suitable base, such as, for example, potassium carbonate, sodium 2-methylpropan-2-olate, tetrabutylammonium fluoride or tribasic potassium phosphate in a suitable solvent, such as, for example, tetrahydrofuran.

Examples of such coupling reactions may be found in the textbook entitled "Metal-Catalyzed Cross-Coupling Reactions", Armin de Meijere (Editor), François Diederich (Editor) September 2004, Wiley Interscience ISBN: 978-3-527-30518-6.

Compounds of general formula I, II, III or VII can be obtained from compounds of general formula IV, V, VI or VIII via a coupling reaction using a reagent of formula Y—$R^3$ in which $R^3$ is defined supra and Y represents a suitable functional group by which the group $R^3$ can be transferred to the $R^{3'}$ bearing carbon atom of compounds of formula IV, V, VI or VIII. Examples of suitable functional groups Y for the use in coupling reactions are given supra for the preparation of compounds of general formula I, IV or VIII from compounds of general formula II, V or IX.

Y in Y—$R^3$ may represent an acidic hydrogen that can be removed by suitable bases, for example sodium hydride, in a suitable solvent, such as DMSO or tetrahydrofuran at temperatures ranging from rt to the boiling point. The resulting nucleophiles, phenolates, can be used to replace $R^{3'}$ in compounds of general formula IV, V, VI or VIII to add phenol ethers to give compounds of general formula I, II, III or VII.

Compounds of general formula I, II, III or VII containing phenolethers can also be built by Ullmann-type coupling reactions in the presence of suitable catalysts, such as, for example, copper based catalysts like copper(II)diacetate in presence of a suitable base, like for example, caesium carbonate staring from compounds of general formula IV, V, VI or VIII in which $R^{3'}$ represents a leaving group such as, for example, an iodine, bromine or chlorine atom. Optionally, suitable ligands like N,N-dimethylglycine or phenyl hydrogen pyrrolidin-2-ylphosphonate can be added.

In the case $Q^1$ represents a leaving group, the introduction of a $R^5$—$CH_2$-group can be achieved by nucleophilic substitution of $Q^1$ in compounds of formula VII, VIII, IX or X i.e. by a reaction with suitable amines $R^5$—$CH_2$—$NH_2$ in the presence of a suitable base, such as, for example DIPEA in a suitable solvent such as N,N-dimethylformamide or 1-methylpyrrolidin-2-one, at temperatures ranging from room temperature to the boiling point of the solvent to give amines of general formula I, IV, V or VI.

In the case $Q^1$ represents a leaving group, the introduction of a $R^5$—$CH_2$-group can also be achieved in a coupling reaction in which $Q^1$ in compounds of formula VII, VIII, IX or X is reacted with suitable amines $R^5$—$CH_2$—$NH_2$ optionally in the presence of a suitable catalyst, such as $Pd_2dba_3$ and BINAP for example, and optionally with a suitable base, such as, for example, sodium tert-butylate in a suitable solvent, such as, for example, N,N-dimethylformamide or 1-methylpyrrolidin-2-one to give amines of general formula I, IV, V or VI.

In the case $Q^1$ represents an optionally protected $NH_2$-group the introduction of a $R^5$—$CH_2$-group, after deprotection to a $NH_2$-group, can be achieved by a reductive amination reaction using an aldehyde of formula O═CHR$^5$, a suitable reducing agent, for example sodium tris(acetato-kappaO)(hydrido)borate or sodium cyanoborohydride in a suitable solvent like, for example, acetic acid at reaction temperatures ranging from room temperature to the boiling point of the solvent. Residues in compounds of formula I, II, III, IV, V, VI, VII, VIII, IX or X can be optionally modified. For example, thioethers can be oxidized using oxidation reagents like 3-chlorobenzenecarboperoxoic acid, oxone or dimethyldioxirane in inert solvents like dichloromethane or acetone, respectively. Depending on the stoichiometric ratio of oxidation reagent to the afore mentioned compounds sulfoxides or sulfones or mixtures thereof will be obtained.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH2 silica gel in combination with a suitable chromatographic system such as a Flashmaster II (Separtis) or an Isolera system (Biotage) and eluents such as, for example, gradients of hexane/EtOAc or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

Example 1

N-cyclopropyl-4-{6-(3-fluoro-4-methoxyphenoxy)-8-[(oxetan-3-ylmethyl)amino]imidazo[1,2-b]pyridazin-3-yl}-2-methylbenzamide

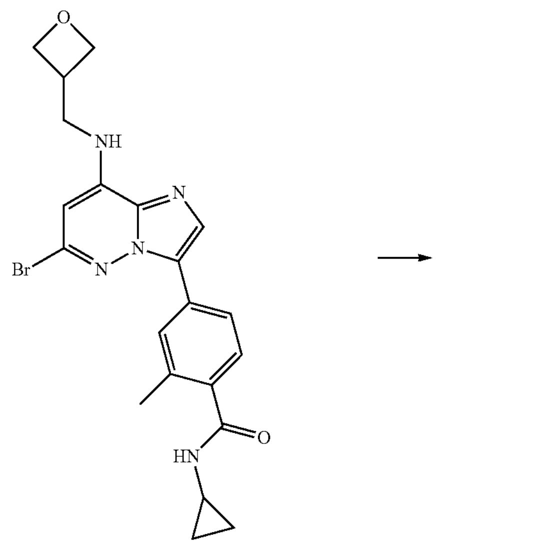

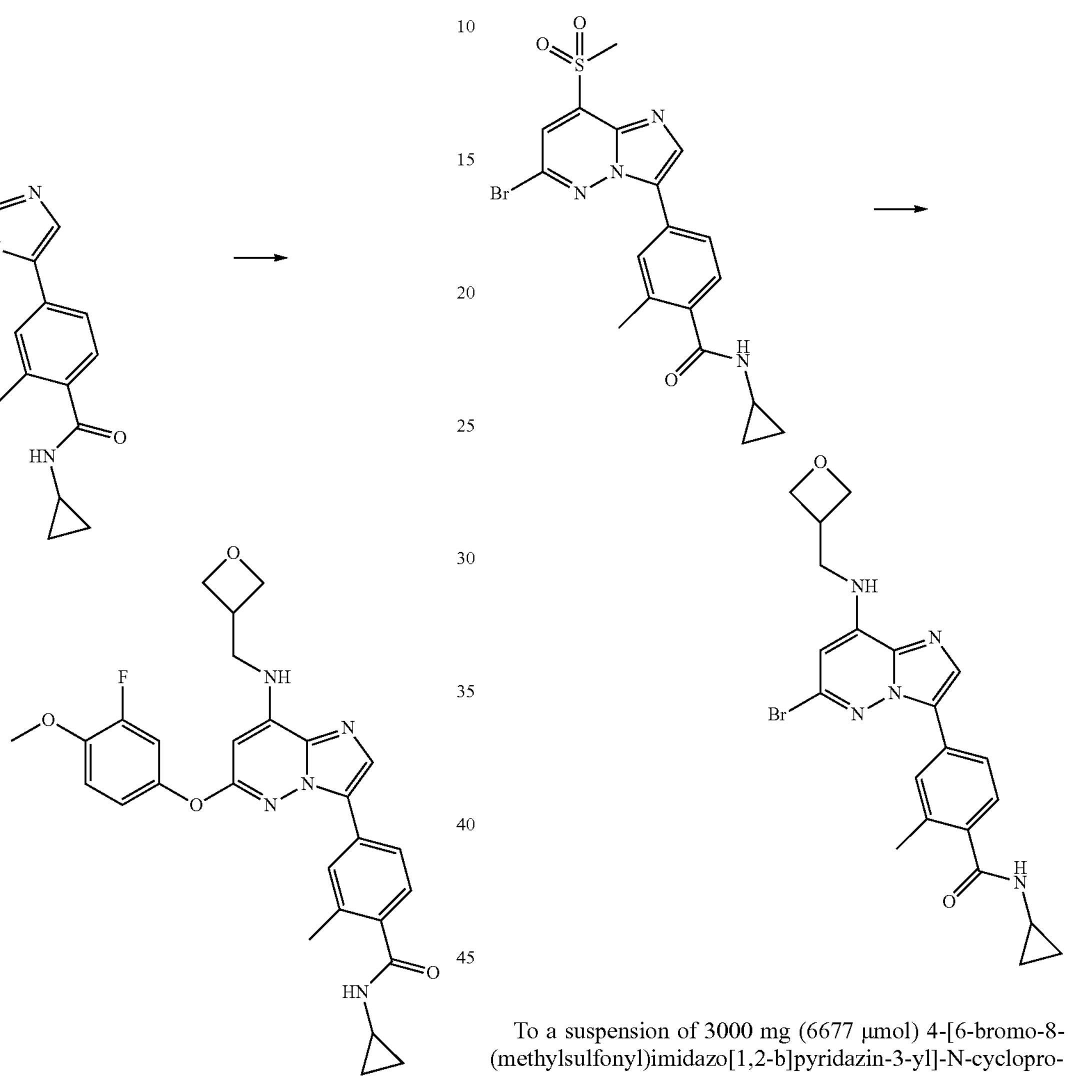

A solution of 128 mg (900 μmol) of 3-fluoro-4-methoxyphenol in 2 mL of dimethylsulfoxide was treated with 36 mg (900 μmol) of sodium hydride and stirred at room temperature for 1 hour. Then 68 mg (150 μmol) of 4-{6-bromo-8-[(oxetan-3-ylmethyl)amino]imidazo[1,2-b]pyridazin-3-yl}-N-cyclopropyl-2-methylbenzamide, which was prepared according to intermediate example 1a, was added and the mixture was heated for 1 h at 130° C. and overnight at 120° C. to give after HPLC purification 17 mg (20%) of the title compound.

$^1$H-NMR (DMSO-d6): δ=0.43-0.50 (2H), 0.59-0.68 (2H), 2.11 (3H), 2.77 (1H), 3.35 (1H), 3.61 (2H), 3.83 (3H), 4.34 (2H), 4.63 (2H), 6.09 (1H), 7.02-7.09 (1H), 7.13-7.25 (2H), 7.30 (1H), 7.61-7.68 (1H), 7.77 (1H), 7.83 (1H), 7.91 (1H), 8.22 (1H) ppm.

Intermediate Example 1a

4-{6-bromo-8-[(oxetan-3-ylmethyl)amino]imidazo[1,2-b]pyridazin-3-yl}-N-cyclopropyl-2-methylbenzamide To a suspension of 3000 mg (6677 μmol) 4-[6-bromo-8-(methylsulfonyl)imidazo[1,2-b]pyridazin-3-yl]-N-cyclopropyl-2-methylbenzamide, which was prepared according to intermediate example 1b in 150 mL of THF were added 873 mg (1002 μmol) 1-(oxetan-3-yl)methanamine and 2589 mg (2003 μmol) DIPEA and the mixture was heated for 72 hours at 60° C. After further addition of 100 mg 1-(oxetan-3-yl) methanamine and heating for 8 h at 60° C., the solvent was removed in vaccuo and the residue was taken up in ethyl acetate and washed with water. The precipitate formed was filtered off to yield 0.99 g (33%) of the title compound. The remaining aqueous phase was reextracted with DCM, and the combined organic phases were evaporated. The residue was triturated with THF at 75° C. to yield another 1.65 g (53%) of the title compound.

$^1$H-NMR (DMSO-d6): δ=0.46-0.53 (2H), 0.61-0.69 (2H), 2.35 (3H), 2.75-2.85 (1H), 3.25 (1H), 3.54-3.69 (2H), 4.31 (2H), 4.62 (2H), 6.45 (1H), 7.36 (1H), 7.84 (1H), 7.90 (1H), 7.94 (1H), 8.12 (1H), 8.30 (1H) ppm.

Intermediate Example 1b

4-[6-bromo-8-(methylsulfonyl)imidazo[1,2-b]pyridazin-3-yl]-N-cyclopropyl-2-methylbenzamide

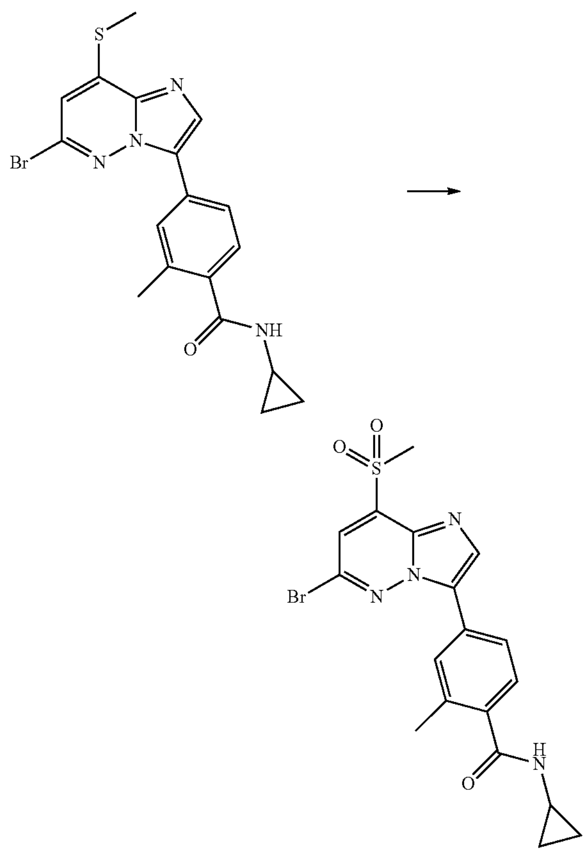

To a solution of 12.5 g (28.75 mmol) 4-[6-bromo-8-(methylsulfanyl)imidazo[1,2-b]pyridazin-3-yl]-N-cyclopropyl-2-methylbenzamide, which was prepared according to intermediate example 1c in 400 mL of DMF were added 53.03 g (86.26 mmol) potassium hydrogen sulfate sulfate (hydroperoxysulfonyl)oxidanide (5:1:1:2) and the mixture was stirred overnight at rt. to give, after aqueous work-up, 8.6 g (60%) of the title compound (impurity is 4-[6-bromo-8-(methylsulfinyl)imidazo[1,2-b]pyridazin-3-yl]-N-cyclopropyl-2-methylbenzamide) UPLC-MS: RT=0.98 min; m/z (ES+) 450.3 [MH+]; required MW=449.3.

Intermediate Example 1c

4-[6-bromo-8-(methylsulfanyl)imidazo[1,2-b]pyridazin-3-yl]-N-cyclopropyl-2-methylbenzamide

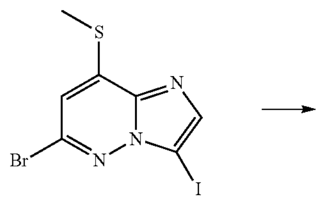

-continued

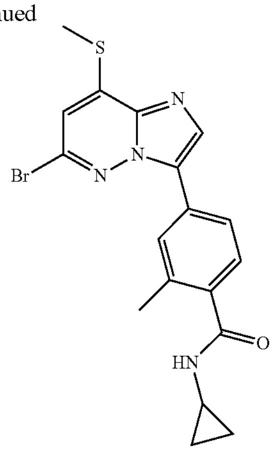

A mixture comprising 55.69 g (150 mmol) 6-bromo-3-iodo-8-(methylsulfanyl)imidazo[1,2-b]pyridazine which was prepared according to intermediate example 1d, 68 g (225 mmol) N-cyclopropyl-2-methyl-4-(4,4,5,5-tetramethyl-1,3,2-dioxaborolan-2-yl)benzamide, which was prepared according to intermediate example 1 g, 11 g (15 mmol) (1,1,-bis(diphenylphosphino)ferrocene)-dichloropalladium (11), 450 mL aqueous 1M potassium carbonate solution and 632 mL tetrahydrofuran was stirred at 60° C. for 12 hours to give, after aqueous workup, 130 g crude product. The residue was triturated with DCM to yield 15.15 g (24%) of the title compound. The filtrate was purified by chromatography to give another 2.65 g (3%) of the title compound.

$^{1}$H-NMR (DMSO-d6): δ=0.47-0.54 (2H), 0.62-0.71 (2H), 2.36 (3H), 2.63 (3H), 2.77-2.85 (1H), 7.17 (1H), 7.40 (1H), 7.85 (1H), 7.90 (1H), 8.12 (1H), 8.31 (1H) ppm.

Intermediate Example 1d 6-bromo-3-iodo-8-(methylsulfanyl)imidazo[1,2-b]pyridazine

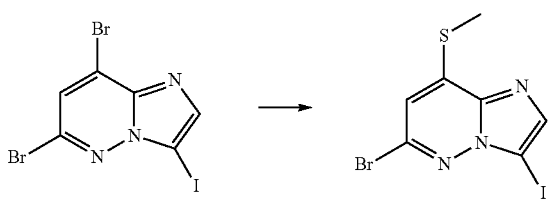

To a solution of 174 g (432 mmol) 6,8-dibromo-3-iodoimidazo[1,2-b]pyridazine which was prepared according to intermediate example 1e in 3.8 L dioxane were added 30.28 g (432 mmol) sodium methanethiolate and the mixture was stirred at 60° C. for 5 days. Further 25 g sodium methanethiolate were added and the mixture was stirred at 80° C. for 2 h. After cooling, the solution was poured on 4 L water Water and the aqueous phase was extracted with ethyl acetate. The organic phase was washed with water, dried over sodium sulphate, filtered and evaporated to give 102 g (64%) of the title compound.

$^{1}$H-NMR (DMSO-d6): δ=6.79 (1H), 7.67 (1H) ppm.

Intermediate Example 1e 6,8-dibromo-3-iodoimidazo[1,2-b]pyridazine

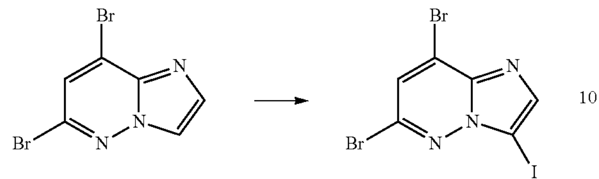

To a mixture comprising 156 g (563 mmol) 6,8-dibromoimidazo[1,2-b]pyridazine which was prepared according to intermediate example 1f, 190 g (1637 mmol) N-iodosuccinimide and 1.3 L chloroform were added 5.5 mL HCl conc and the suspension was heated at 70° C. overnight. The precipitate was filtered off and triturated with diisopropylether to give 119 g (52%) of the title compound.

$^1$H-NMR (DMSO-d6): δ=7.92 (1H), 8.00 (1H) ppm.

Intermediate Example 1f 6,8-dibromoimidazo[1,2-b]pyridazine

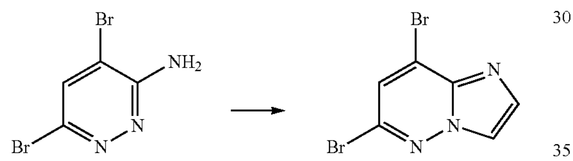

A mixture comprising 235 g (931 mmol) 4,6-dibromopyridazin-3-amine which was prepared according to intermediate example 1 g, 421 mL (2792 mmol) 2-bromo-1,1-diethoxyethane, 2.93 L water and 227 mL THF was heated at 125° C. for h and at rt overnight. The solution was neutralized by addition of solid $NaHCO_3$, the precipitate was filtered off, washed with water and dried to give 156 g (80%) of the title compound as a brownish solid.

$^1$H-NMR (DMSO-d6): δ=7.81 (1H), 8.40 (1H) ppm.

Intermediate Example 1 g 6,8-dibromoimidazo[1,2-b]pyridazine

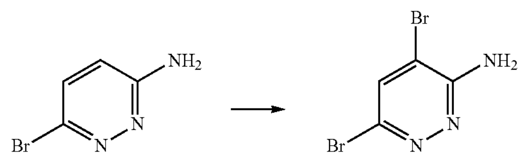 [SMILES: Nc1ccc(Br)nn1 ; Nc1nnc(Br)cc1Br]

To a mixture comprising 285 g (1638 mmol) 6-bromopyridazin-3-amine which was prepared according to intermediate example 1 h, 275 g (3276 mmol) $NaHCO_3$ and 2815 mL MeOH was dropwise added 85 mL (1638 mmol) bromine at rt and it was stirred at rt overnight. After further addition of 34 mL (655 mmol) bromine and 55 g (655 mmol) $NaHCO_3$, the mixture was stirred overnight again. The solvent was reduced to about 1000 mL and the mixture was poured on 5 L of water. The precipitate was filtered off, washed with water and dried give 411 g (99%) of the title compound.

$^1$H-NMR ($CDCl_3$): δ=6.14 (1H), 9.92 (2H) ppm.

Intermediate Example 1 h 6-bromopyridazin-3-amine

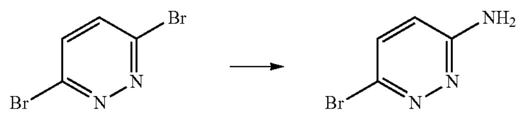 [SMILES: Brc1ccc(Br)nn1 ; Nc1ccc(Br)nn1]

A solution of 250 g (1.05 mol) 3,6-dibromopyridazine in 1.2 L 25% aqueous ammonia was heated to 100° C. at 11.7 bar overnight in an autoclave. After cooling, the precipitate was filtered off, washed with water and dried to give 137 g (75%) of the title compound.

$^1$H-NMR (DMSO-d6): δ=6.58 (1H), 6.69 (2H), 7.41 (1H) ppm.

Intermediate Example 1i

N-cyclopropyl-2-methyl-4-(4,4,5,5-tetramethyl-1,3,2-dioxaborolan-2-yl)benzamide

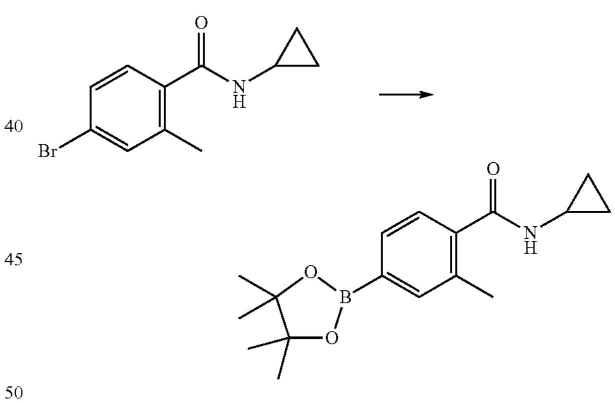

To a solution of 260 g (1.02 mol) 4-bromo-N-cyclopropyl-2-methylbenzamide which was prepared according to intermediate example 1j in 2 L dioxane at 23° C. were added 390 g bis-(pinacolato)-diboron, 19.5 g 2-dicyclohexylphosphino-2',4',6'-triisopropylbiphenyl, 150.g potassium acetate and 9.37 g tris-(dibenzylidenaceton)-dipalladium(0) and the mixture was refluxed for 6 h. After cooling to 23° C., water and ethyl acetate were added and the mixture stirred for 15 min. The organic phase was washed with water, dried over sodium sulfate, filtered and evaporated. The residue was purified by chromatography to give 308 g (56%) of the title compound.

$^1$H-NMR (300 MHz, $CDCl_3$): δ=0.59 (2H), 0.85 (2H), 1.33 (6H), 2.41 (3H), 2.87 (1H), 5.94 (1H), 7.28 (1H), 7.60 (1H), 7.63 (1H) ppm.

Intermediate Example 1j

4-Bromo-N-cyclopropyl-2-methylbenzamide

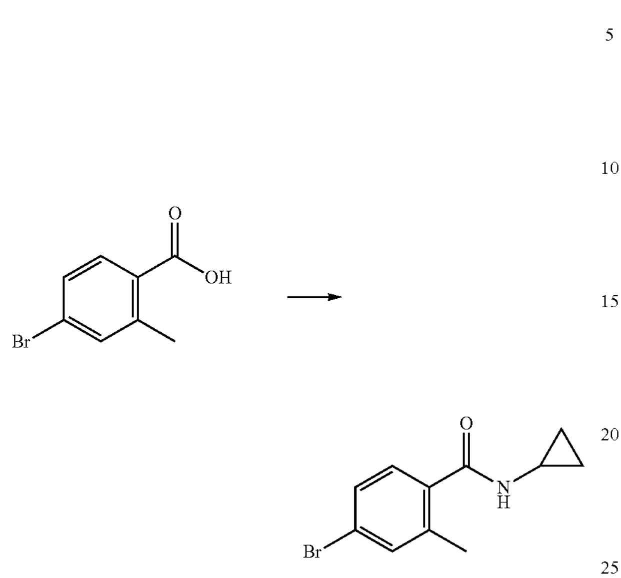

To a stirred solution of 300 g (1.4 mol) 4-bromo-2-methylbenzoic acid in 8.4 L dichloromethane at 23° C. were added 79.6 g cyclopropanamine and 320.9 g EDC. After stirring overnight, the solution was washed with water and the aqueous phase was extracted with dichloromethane. The combined organic phases were dried over sodium sulfate, filtered and evaporated. The remaining solid was triturated with diisopropyl ether, filtered, washed and dried in vaccuo to yield 260 g (73%) of the title compound.

Example 2

N-cyclopropyl-4-{6-(2,3-difluoro-4-methoxyphenoxy)-8-[(3,3,3-trifluoropropyl)amino]imidazo[1,2-b]pyridazin-3-yl}-2-methylbenzamide

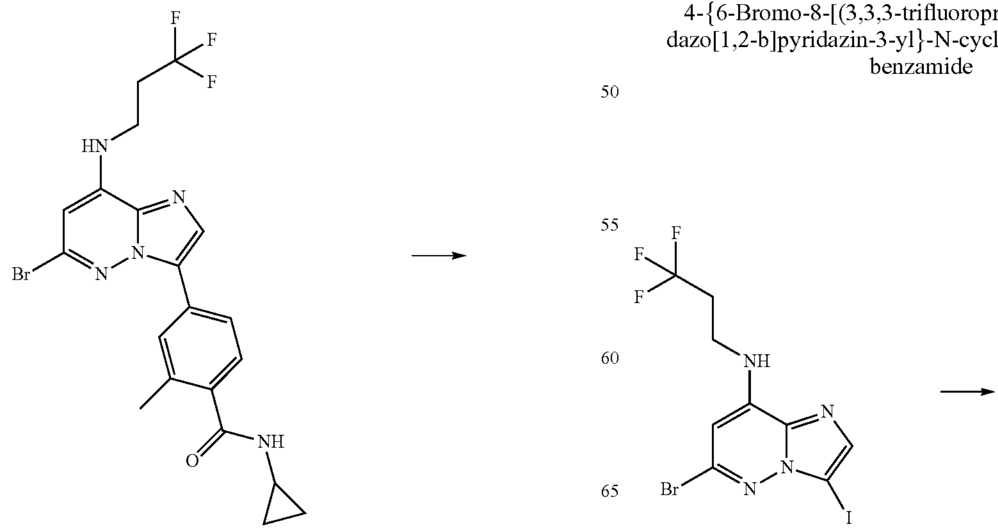

-continued

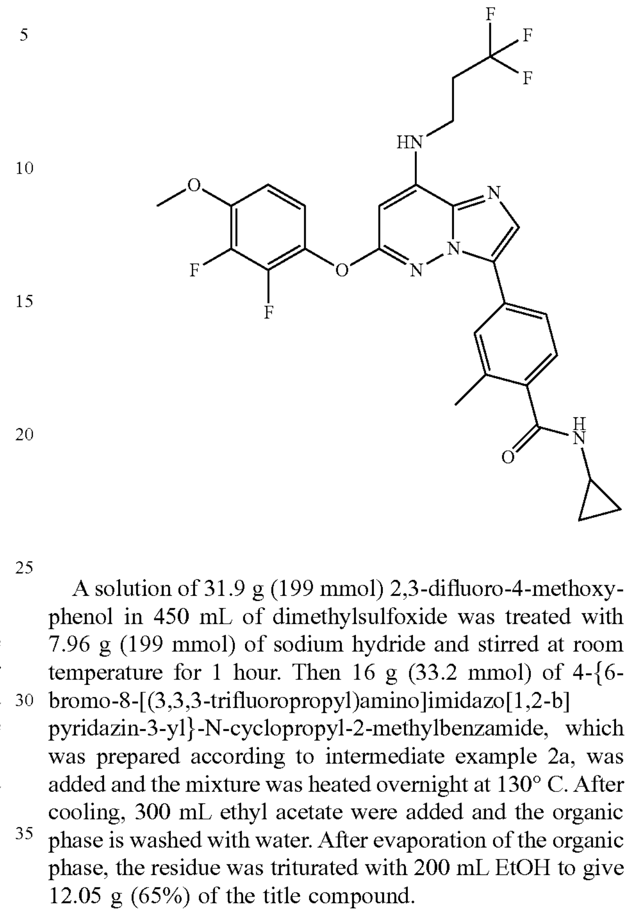

A solution of 31.9 g (199 mmol) 2,3-difluoro-4-methoxyphenol in 450 mL of dimethylsulfoxide was treated with 7.96 g (199 mmol) of sodium hydride and stirred at room temperature for 1 hour. Then 16 g (33.2 mmol) of 4-{6-bromo-8-[(3,3,3-trifluoropropyl)amino]imidazo[1,2-b]pyridazin-3-yl}-N-cyclopropyl-2-methylbenzamide, which was prepared according to intermediate example 2a, was added and the mixture was heated overnight at 130° C. After cooling, 300 mL ethyl acetate were added and the organic phase is washed with water. After evaporation of the organic phase, the residue was triturated with 200 mL EtOH to give 12.05 g (65%) of the title compound.

$^1$H-NMR (DMSO-d6): δ=0.47-0.53 (2H), 0.62-0.70 (2H), 2.11 (3H), 2.72 (2H), 2.80 (1H), 3.64 (2H), 3.92 (3H), 6.22 (1H), 7.12 (1H), 7.18 (1H), 7.27 (1H), 7.63 (1H), 7.72 (1H), 7.75-7.81 (1H), 7.97 (1H), 8.24 (1H) ppm.

Intermediate Example 2a

4-{6-Bromo-8-[(3,3,3-trifluoropropyl)amino]imidazo[1,2-b]pyridazin-3-yl}-N-cyclopropyl-2-methylbenzamide -continued

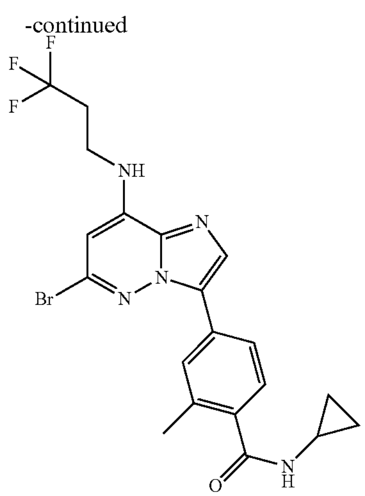

A mixture comprising 127 g (292 mmol) 6-bromo-3-iodo-N-(3,3,3-trifluoropropyl)imidazo[1,2-b]pyridazin-8-amine which was prepared according to intermediate example 2b, 95.93 g (438 mmol) [4-(cyclopropylcarbamoyl)-3-methylphenyl]boronic acid which was prepared according to intermediate example 2c, 23.8 g (29 mmol) (1,1,-bis(diphenylphosphino)ferrocene)-dichloropalladium (II), 438 mL aqueous 1M potassium carbonate solution and 973 mL tetrahydrofuran was stirred at 80° C. for 8 hours and further 6 days at 60° C. Ethyl acetate was added to the separated organic phase and the mixture was washed with water. After filtration over ALLOX, the organic phase was evaporated and the residue was triturated with 200 mL EtOH to give 71.2 g (51%) of the title compound.

$^1$H-NMR (DMSO-d6): δ=0.48-0.58 (2H), 0.63-0.73 (2H), 2.38 (3H), 2.68 (2H), 2.83 (1H), 3.61 (2H), 6.49 (1H), 7.40 (1H), 7.87 (1H), 7.93 (1H), 7.96-8.04 (2H), 8.32 (1H) ppm.

Intermediate Example 2b

6-Bromo-3-iodo-N-(3,3,3-trifluoropropyl)imidazo[1,2-b]pyridazin-8-amine

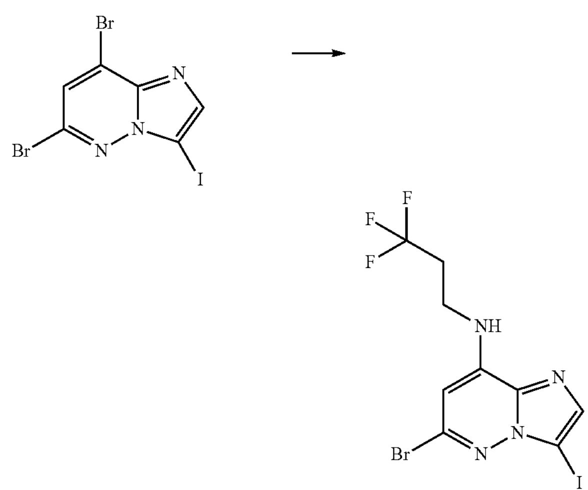

To a solution of 119 g 295 mmol) 6,8-dibromo-3-iodoimidazo[1,2-b]pyridazine which was prepared according to intermediate example 1e in 800 mL THF were added 66.8 g (590.8 mmol) 3,3,3-trifluoropropan-1-amine and the mixture was stirred at 80° C. for 2 h and at 50° C. overnight. The solution was evaporated, 600 mL ethyl acetate were added and the mixture was washed with water. The organic phase was dried and evaporated to give 127 g (99%) of the title compound.

$^1$H-NMR (DMSO-d6): δ=2.63 (2H), 3.55 (2H), 6.43 (1H), 7.59 (1H), 7.89-7.98 (1H) ppm.

Intermediate Example 2c

[4-(cyclopropylcarbamoyl)-3-methylphenyl]boronic acid

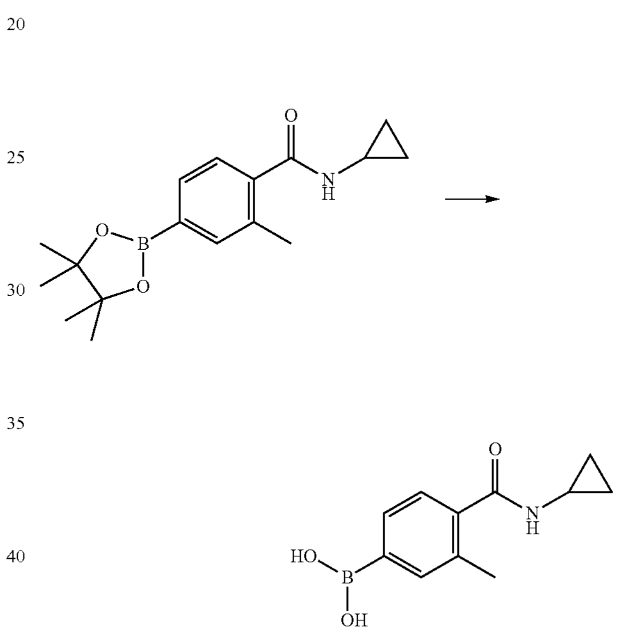

To a solution of N-cyclopropyl-2-methyl-4-(4,4,5,5-tetramethyl-1,3,2-dioxaborolan-2-yl)benzamide (20.2 g, 67.13 mol) which was prepared according to intermediate example 1i in acetone (300 mL) at rt was added sodium periodate (43.1 g, 201.40 mol) and ammonium acetate (134.26 mol, 134 mL 1M aqueous solution) and the mixture was stirred for 3 h. More water was added (120 mL), and the mixture was stirred at 40° C. for 2 h more. After addition of 4 N HCl (32 mL), the organic phase was removed in vaccuo and the reminder was extracted with ethyl actate. The organic phase was washed with sat. sodium chloride solution, filtered through a Whatman filter and evaporated. The residue was redissolved in toluene and evaporated (two times) to yield 14.59 g (94.3%) [4-(cyclopropylcarbamoyl)-3-methylphenyl]boronic acid: $^1$H-NMR (300 MHz, $d_6$-DMSO): δ=8.21 (1H), 8.04 (2H), 7.56 (2H), 7.17 (1H), 2.77 (1H), 2.25 (3H), 0.62 (2H), 0.47 (2H) ppm.

Example 3

N-cyclopropyl-4-{6-(2,3-difluoro-4-methoxyphenoxy)-8-[(tetrahydro-2H-pyran-4-ylmethyl)amino]imidazo[1,2-b]pyridazin-3-yl}-2-methylbenzamide

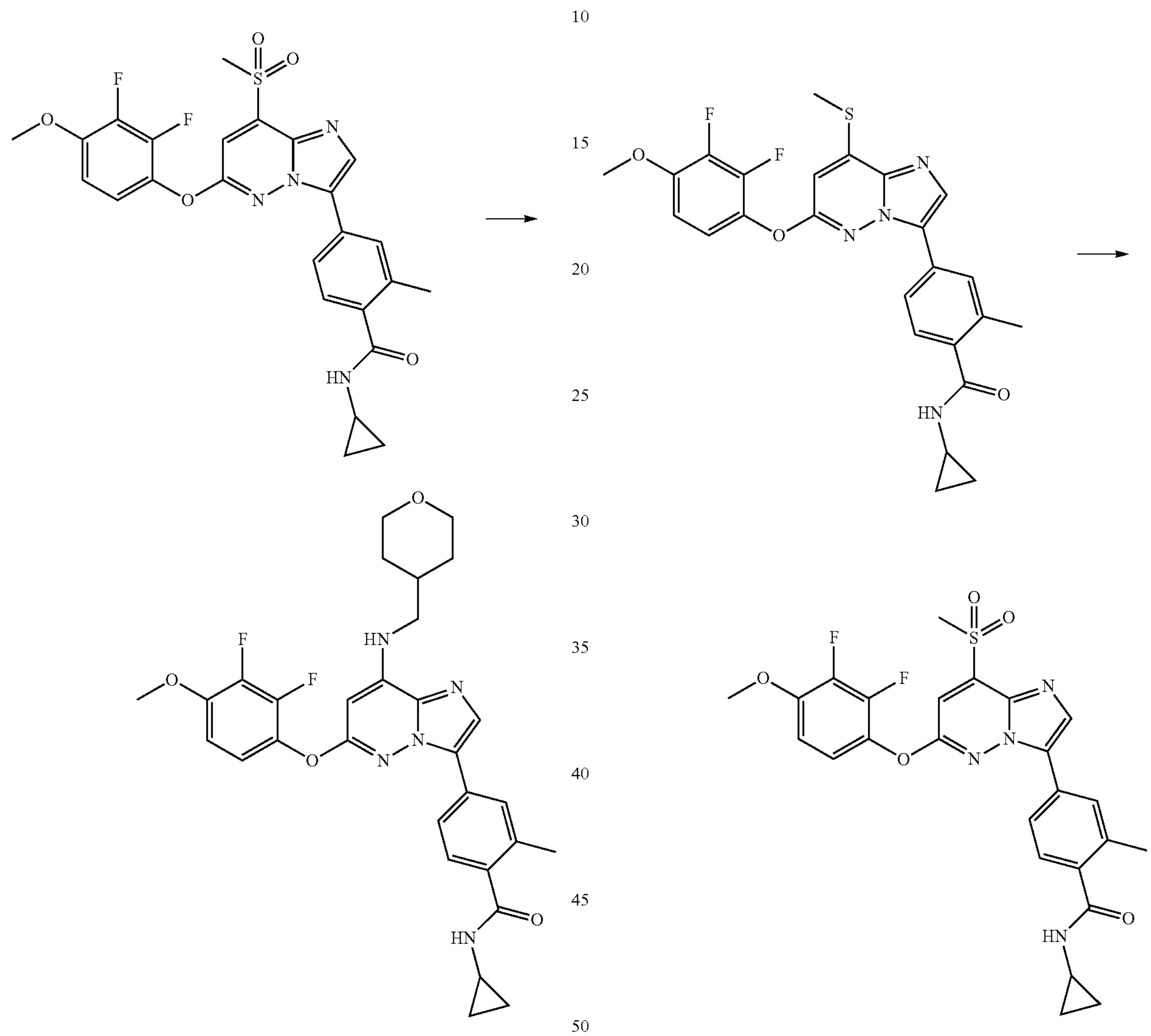

To a solution of 52 mg (0.1 mmol) N-cyclopropyl-4-[6-(2,3-difluoro-4-methoxyphenoxy)-8-(methylsulfonyl)imidazo[1,2-b]pyridazin-3-yl]-2-methylbenzamide which was prepared according to intermediate example 3a in NMP (2 mL) at rt was 1-(tetrahydro-2H-pyran-4-yl)methanamine (35 mg, 0.3 mmol) and DIPEA (0.3 mmol, 51 µL) and the mixture was stirred at 110° C. for 72 h to give after HPLC purification 26.9 mg (47%) of the title compound $^{1}$H-NMR (DMSO-d6): δ=0.43-0.50 (2H), 0.58-0.69 (2H), 1.22 (2H), 1.62 (2H), 1.86-2.02 (1H), 2.04-2.11 (3H), 2.77 (1H), 3.19-3.30 (4H), 3.82 (2H), 3.89 (3H), 6.16 (1H), 7.03-7.13 (1H), 7.15 (1H), 7.20-7.30 (1H), 7.57-7.63 (1H), 7.69 (1H), 7.80 (1H), 7.93 (1H), 8.24 (1H) ppm.

Intermediate Example 3a

N-cyclopropyl-4-[6-(2,3-difluoro-4-methoxyphenoxy)-8-(methylsulfonyl)imidazo[1,2-b]pyridazin-3-yl]-2-methylbenzamide 986 mg (1986 µmol) N-cyclopropyl-4-[6-(2,3-difluoro-4-methoxyphenoxy)-8-(methylsulfanyl)imidazo[1,2-b]pyridazin-3-yl]-2-methylbenzamide which was prepared according to intermediate example 3b were transformed in analogy to intermediate example 1b to give after working up 1040 mg (99%) of the title compound.

$^{1}$H-NMR (DMSO-d6): δ=0.44-0.51 (2H), 0.61-0.69 (2H), 2.11 (3H), 2.73-2.84 (1H), 3.66 (3H), 3.91 (3H), 7.13-7.21 (1H), 7.23 (1H), 7.33-7.42 (1H), 7.64-7.70 (3H), 8.30 (1H), 8.40 (1H) ppm.

Intermediate Example 3b

N-cyclopropyl-4-[6-(2,3-difluoro-4-methoxyphenoxy)-8-(methylsulfanyl)imidazo[1,2-b]pyridazin-3-yl]-2-methylbenzamide

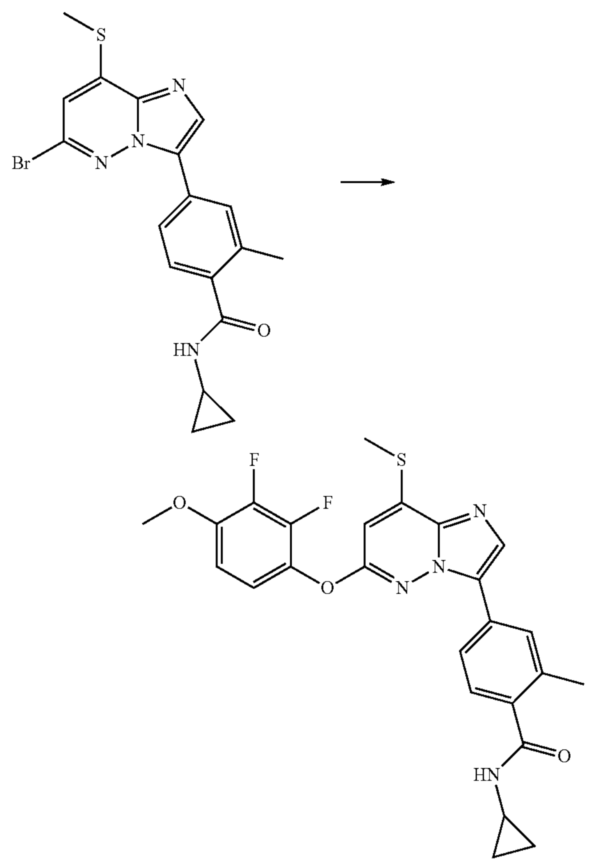

3.1 g (7428 μmol) 4-[6-bromo-8-(methylsulfanyl)imidazo[1,2-b]pyridazin-3-yl]-N-cyclopropyl-2-methylbenzamide which was prepared according to intermediate example 1b were transformed in analogy to example 2 using 2,3-difluoro-4-methoxyphenol to give after working up and purification 1010 mg (27%) of the title compound.

$^1$H-NMR (DMSO-d6): δ=0.44-0.50 (2H), 0.59-0.70 (2H), 2.09 (3H), 2.67 (3H), 2.73-2.83 (1H), 3.90 (3H), 7.06 (1H), 7.14 (1H), 7.19 (1H), 7.31 (1H), 7.58-7.65 (1H), 7.67 (1H), 8.09 (1H), 8.26 (1H) ppm.

The set of compounds given in Table 1 surprisingly exhibits a superior overall profile with respect to Mps-related activity in a functional assay (Spindle Assembly Checkpoint Assay), antiproliferative activity (Proliferation Assay with HeLa cells), metabolic stability (in vitro metabolic stability in rat hepatocytes) and drug-drug interaction potential (inhibition of liver enzyme CYP3A4). To further assess irreversible CYP3A4 inhibition potential, the partion ratio of the compounds was determined, which is indicates how many substrate turnovers can be made by the enzyme prior to inactivation.

Selection criteria were Activity in Spindle Assembly Checkpoint Assay <1.0 nM, Activity in Proliferation Assay with HeLa cells <25 nM, in vitro metabolic stability in rat hepatocytes Fmax ≥39% and inhibition of liver enzyme CYP3A4 ≥5 μM, and a partion ratio ≥10.

In Table 1 Ref. is a reference compound disclosed in example 80 of WO2012/032031A1: (N-cyclopropyl-4-{6-(3-fluorophenoxy)-8-[(3,3,3-trifluoropropyl)amino]imidazo[1,2-b]pyridazin-3-yl}-2-methylbenzamide). The compound Ref. is structurally very similar to the compounds of the present invention, in particular to the compound of formula (B). Despite the structural similarity the compounds of the present invention show superior overall profile. From the teaching of WO2012/032031A1 one of ordinary skill in the art is not able to derive the superior profile of the compounds of the present invention.

TABLE 1

| Example | SAC [nM] | HeLa [nM] | Fmax rat hep [%] | CYP3A4 [μM] | CYP3A4 partition ratio |
|---|---|---|---|---|---|
| 1 | 0.97 | 2.9 | 44 | >5 | 105 |
| 2 | 0.62 | 7.8 | 72 | >10 | 18 |
| 3 | 0.08 | 18.1 | 39 | >10 | 33 |
| Ref. | 0.52 | 23 | 38 | >10 | 3 |

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)— Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);
stiffening agents (examples include but are not limited to cetyl alcohol, cetyl esters wax, microcrystalline wax, paraffin, stearyl alcohol, white wax and yellow wax);
suppository bases (examples include but are not limited to cocoa butter and polyethylene glycols (mixtures));
surfactants (examples include but are not limited to benzalkonium chloride, nonoxynol 10, oxtoxynol 9, polysorbate 80, sodium lauryl sulfate and sorbitan mono-palmitate);
suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);
sweetening agents (examples include but are not limited to aspartame, dextrose, glycerol, mannitol, propylene glycol, saccharin sodium, sorbitol and sucrose);
tablet anti-adherents (examples include but are not limited to magnesium stearate and talc);
tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);
tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);
tablet direct compression excipients (examples include but are not limited to dibasic calcium phosphate);
tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);
tablet glidants (examples include but are not limited to colloidal silica, corn starch and talc);
tablet lubricants (examples include but are not limited to calcium stearate, magnesium stearate, mineral oil, stearic acid and zinc stearate);
tablet/capsule opaquants (examples include but are not limited to titanium dioxide);
tablet polishing agents (examples include but are not limited to carnuba wax and white wax);
thickening agents (examples include but are not limited to beeswax, cetyl alcohol and paraffin);
tonicity agents (examples include but are not limited to dextrose and sodium chloride);
viscosity increasing agents (examples include but are not limited to alginic acid, bentonite, carbomers, carboxymethylcellulose sodium, methylcellulose, polyvinyl pyrrolidone, sodium alginate and tragacanth); and
wetting agents (examples include but are not limited to heptadecaethylene oxycetanol, Lecithins, sorbitol monooleate, polyoxyethylene sorbitol monooleate, and polyoxyethylene stearate).

Pharmaceutical compositions according to the present invention can be illustrated as follows:

Sterile IV Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised Powder for IV Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The additional pharmaceutical agent can be 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, Lanreotide, lapatinib, lenalidomide, lenograstim, lentinan, letrozole, Leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Preferably, the additional pharmaceutical agent is selected from: afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulfate, letrozole, leucovorin, leuprolide, leuprolide acetate, Levamisole, Levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib (BAY 43-9006), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, and zoledronic acid or combinations thereof.

Optional anti-hyper-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, epothilone, an epothilone derivative, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, Labetuzumab, alpha-particle-emitting radioisotope-llinked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

The compounds of the invention may also be combined with biological therapeutic agents, such as antibodies (e.g. avastin, rituxan, erbitux, herceptin), or recombinant proteins.

The compounds of the invention may also be in combination with antiangiogenesis agents, such as, for example, with avastin, axitinib, DAST, recentin, sorafenib or sunitinib. Combinations with inhibitors of proteasomes or mTOR inhibitors, or anti-hormones or steroidal metabolic enzyme inhibitors are also possible.

Generally, the use of cytotoxic and/or cytostatic agents in combination with a compound or composition of the present invention will serve to:

(1) yield better efficacy in reducing the growth of a tumour or even eliminate the tumour as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumour progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of formula (A), (B) or (C), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of formula (A), (B) or (C), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of formula (A), (B) or (C) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers. Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's Lymphoma, cutaneous T-cell Lymphoma, Burkitt Lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et at. New Engl. J. Med. 1994, 331, 1480; Peer et at. Lab. Invest. 1995, 72, 638], age-related macular degeneration [AMD; see, Lopez et at. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological assay: Proliferation Assay Cultivated tumour cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumour cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The IC50 values were determined by means of a 4 parameter fit using the company's own software.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (C-terminus in amide form, purchased from Biosynthan GmbH, Berlin) was used.

For the assay 50 nL of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM $MgCl_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 µl assay volume). The reaction was stopped by the addition of 3 µl of a solution of HTRF detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho(Ser/Thr)-Europium-antibody [#AD0180, PerkinElmer LAS, Rodgau-Jügesheim, Germany].

The resulting mixture was incubated 1 h at 22° C. to allow the binding of the phosphorylated peptide to the anti-phospho(Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an in-house software.

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumour cell line HeLa (ATCC CCL-2) were plated at a density of 2500 cells/well in a 384-well microtiter plate in 20 μl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 μl/well nocodazole at a final concentration of 0.1 μg/ml were added to cells. After 24 h incubation, cells were arrested at G2/M phase of the cell cycle progression. Test compounds solubilised in dimethyl sulfoxide (DMSO) were added at various concentrations (0 μM, as well as in the range of 0.005 μM-10 μM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 μl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 μl/well HOECHST 33342 dye solution (5 μg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the $IC_{50}$ value for each tested compound.

Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 ml falcon tubes and centrifuged at 50×g for 3 min at room temperature. The cell pellet was resuspended in 30 ml WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0\times10^6$ vital cells/mL. The test compound was added to a final concentration of 1 μM. During incubation, the hepatocyte suspensions were continuously shaken and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated. The following parameter values were used: Liver blood flow—4.2 L/h/kg rat; specific liver weight—32 g/kg rat body weight; liver cells in vivo—$1.1\times10^8$ cells/g liver, liver cells in vitro—$0.5\times10^6$/ml.

Determination of Inhibitory Potential on Human CYP3A4

The potential of the test compound to act as a competitive inhibitor of CYP3A4 was evaluated in in vitro assays, using human liver microsomes and the reference substrate midazolam. The test compound was solved in acetonitrile. Human liver microsomal preparation (pool of HLM) was applied for the assay. A stock solution of the test compound was added to phosphate buffer containing EDTA, NADP, glucose 6-phosphate, and glucose 6-phosphate dehydrogenase. This mixture was sequentially diluted on a Genesis Workstation (Tecan, Crailsheim, FRG). After pre-warming, reaction was initiated by addition of a mixture of probe substrate (midazolam). Finally, the incubation mixtures contained human liver microsomes at protein concentration of 60 μg/mL, NADPH-regenerating system (1 mM NADP, 5.0 mM glucose 6-phosphate, glucose 6-phosphate dehydrogenase (1.5 U/mL), 1.0 mM EDTA, the test compound at 6 different concentrations, 2.5 μM midazolam as probe substrate, and phosphate buffer (50 mM, pH 7.4) in a total volume of 200 μL. Incubations were performed on a Genesis Workstation (Tecan, Crailsheim, FRG) in 96-well plates (Microtiter plate, 96-well plate) at 37° C. Stock solution of probe substrate was prepared in water (midazolam 10 mM). Ketoconazole was used as positive control of a direct-acting inhibitor. The reference samples (substrate, but no inhibitor)

were incubated in parallel in sextuple and contained the same amount of solvent as the test incubations. Reactions were stopped by addition of 100 μL acetonitrile containing the internal standard. Precipitated proteins were removed by centrifugation of the well plate, supernatants were analyzed by LC-MS/MS.

The CYP3A4-mediated metabolic activity in the presence of the test compounds was expressed as percentages of the corresponding reference value. A sigmoid-shaped curve was fitted to the data to calculate the enzyme inhibition parameter IC50 using a nonlinear least-squares regression analysis of the plot of percent control activity versus concentration of the test inhibitor. Observing less than 50% inhibition, the data were not extrapolated; hence, IC50 were reported as being greater than the highest concentration of the test compound applied.

Determination of Mechanism-Based Inhibition of Human CYP3A4

Mechanism-based (irreversible) inhibition of CYP3A4 was investigated in vitro using either human liver microsomes (0.5 mg/mL) or recombinant CYP3A4 isoform (50 or 100 pmol/mL). The test compound was incubated at 37° C. in a concentration-NADPH-, and time-dependent setting. Therefore, the test compound was incubated at 4 different concentrations (e.g.: 1, 2, 5, 10 μM) in the presence of NADPH (1 M) and regenerating system in phosphate-buffered saline (0.05 mM, pH 7.4) The highest concentration of test compound was incubated without NADPH and therefore served as the NADPH-deficient control. In addition, acetonitrile as a vehicle control (negative control) and mibefradil as positive control for irreversible CYP3A4 inactivation were also included using identical assay conditions.

Each mixture was incubated with the enzyme (preincubation) for up to 50 minutes. In the beginning and every 10 minutes an aliquot of this incubation mixture was removed and further diluted by a factor of 10-50 (preferred 25) into a new incubation containing NADPH (1 mM) and 150 μM testosterone as the specific substrate for CYP3A4 (main incubation) and allowed to incubate an additional amount of time (e.g. 10 to 20 min) to generate the isoform specific metabolite for the final enzyme activity assessment.

Afterwards, the reaction in the main incubation was stopped by the addition of acetonitrile (containing an internal standard), the protein was allowed to precipitate by placing the mixture into an ice bath. Subsequently, the mixture was centrifuged to pelletize the protein and the supernatants were analyzed by HPLC-MS for the isoform specific metabolite e.g. 6-13 hydroxytestosterone and the remaining amount of the test compound.

The remaining enzyme activity was normalized to the initial activity at time 0 min, and then displayed in a semilogarithmic plot dependent on preincubation time. In parallel the turnover of the substrate was plotted against the preincubation time. From these data kinetic parameters, such as the efficiency of this process expressed by the partition ratio r (number of inactivator molecules metabolized by protein molecule of CYP3A4 inactivated) were calculated. For a general description how to determine the partition ratio see R. B. Silverman Methods Enzymol 1995, 249, 240-283.

The invention claimed is:

1. A compound of formula (A), (B) or (C):

(A)

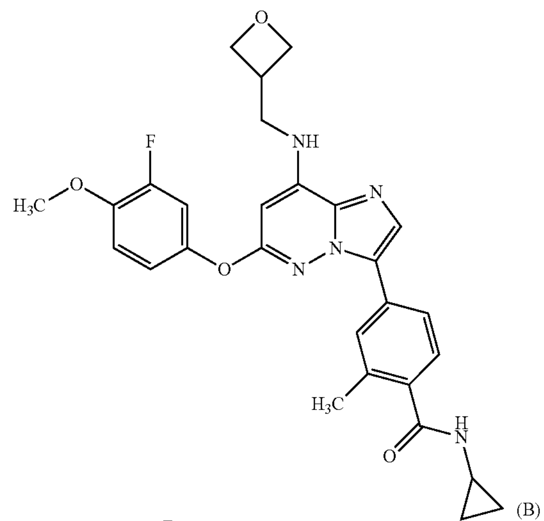

(B)

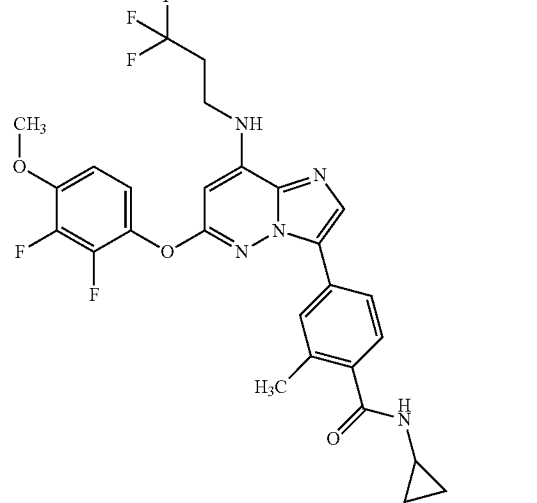

(C)

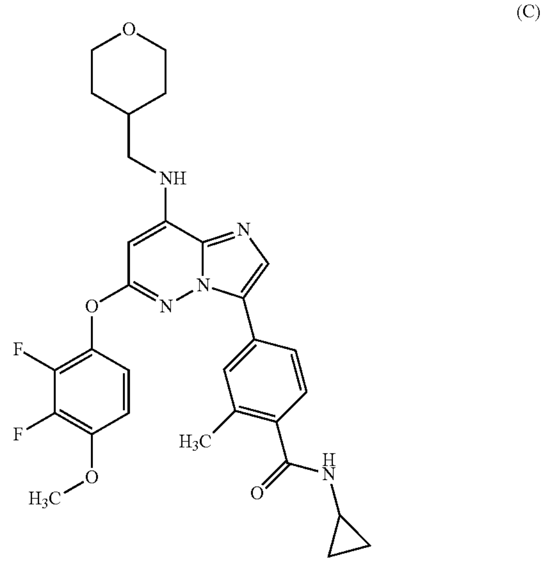

or a stereoisomer, a tautomer, an N-oxide, a hydrate, a solvate, or a salt thereof, or a mixture of same.

2. A pharmaceutical composition comprising a compound according to claim 1, or a stereoisomer, a tautomer, an N-oxide, a hydrate, a solvate, or a salt thereof, particularly a pharmaceutically acceptable salt thereof, or a mixture of same, and a pharmaceutically acceptable diluent or carrier.

3. A pharmaceutical combination comprising:

a compound according to claim 1, or a stereoisomer, a tautomer, an N-oxide, a hydrate, a solvate, or a pharmaceutically acceptable salt thereof, or a mixture of same;

and one or more agents selected from: a taxane, Docetaxel, Paclitaxel, or Taxol; an epothilone, Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2"-deoxyadenosine; Thioguanine; an anti-androgen, Flutamide, Cyproterone acetate, or Bicalutamide; Bortezomib; a platinum derivative, Cisplatin, or Carboplatin; Chlorambucil; Methotrexate; and Rituximab.

4. A method of preparing a compound according to claim 1, comprising reacting an intermediate compound of formula (A1), (B1) or (C1):

(A1)

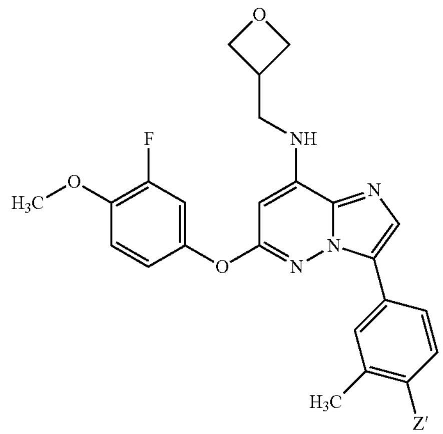

(B1)

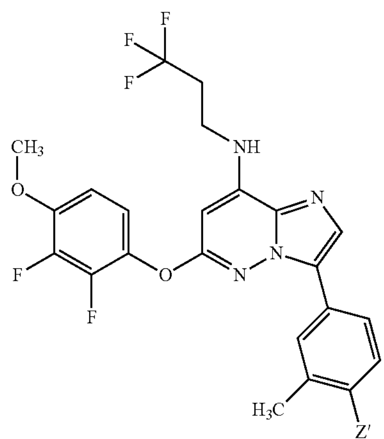

-continued (C1)

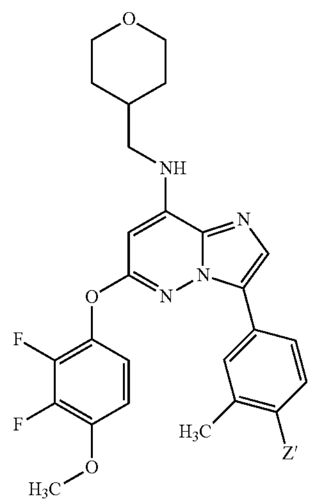

in which Z' represents a group selected from: —C(═O)OH and —C(═O)O—($C_1$-$C_6$-alkyl);

with a compound of formula Ib:

Ib

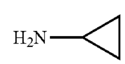

thereby giving, upon optional deprotection, a compound of formula (A), (B) or (C) as defined in claim 1.

5. A method of preparing a compound according to claim 1, comprising reacting an intermediate compound of formula (A2), (B2) or (C2):

(A2)

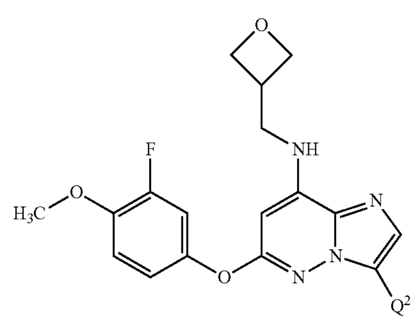

(B2)

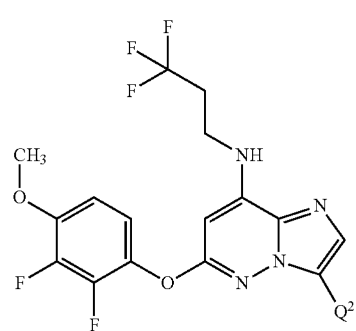

-continued (C2)

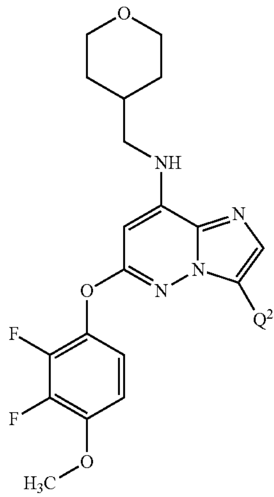

in which $Q^2$ is a leaving group;

with a compound of formula IIa:

IIa in which Y is a substituent which is displaced in a coupling reaction;

thereby giving, upon optional deprotection, a compound of formula (A), (B) or (C), as defined in claim 1.

6. A method of preparing a compound according to claim 1, comprising reacting an intermediate compound of formula (A3), (B3) or (C3):

(A3)

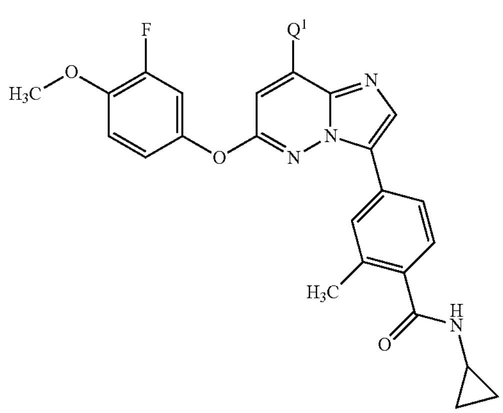

-continued (B3)

(C3)

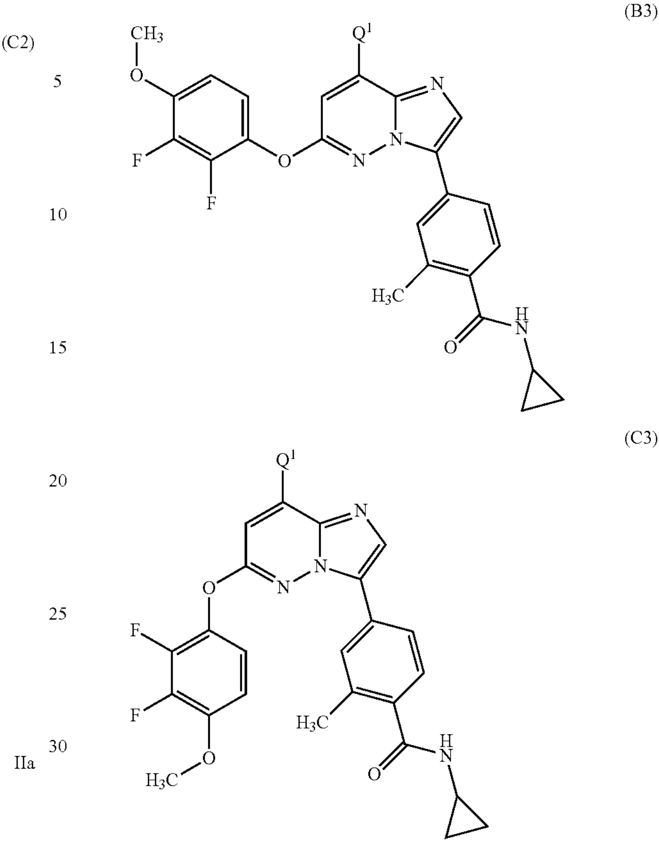

in which $Q^1$ is a leaving group;

with a compound of formula (A4), (B4) or (C4):

(A4)

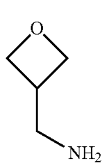

(B4)

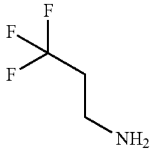

(C4)

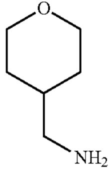

thereby giving, upon optional deprotection, a compound of formula (A), (B) or (C), as defined in claim 1.

7. A method of preparing a compound according to claim 1, comprising reacting an intermediate compound of formula (A5), (B5) or (C5):

(A5)
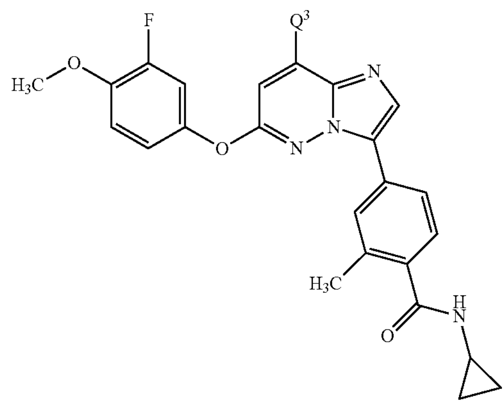
(B5)
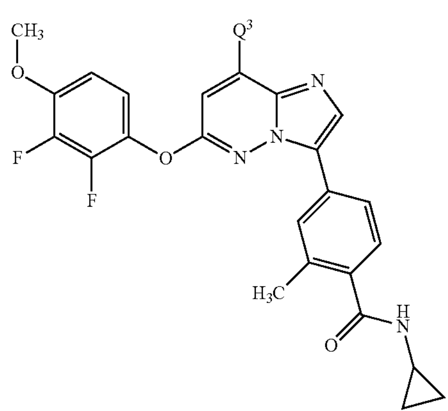
(C5)
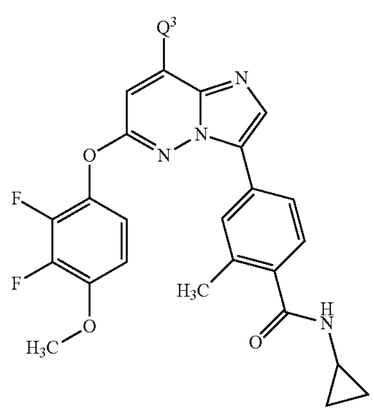
in which $Q^3$ is an optionally protected $NH_2$-group; with a compound of formula (A6), (B6) or (C6):
(A6)
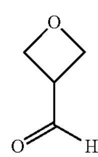
-continued
(B6)
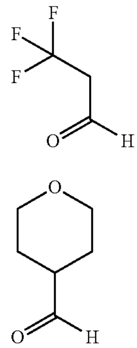
(C6)
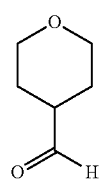
thereby giving, after reduction of the imine, and upon optional deprotection, a compound of formula (A), (B) or (C), as defined in claim 1.
8. A method of preparing a compound according claim 1, comprising reacting an intermediate compound of formula (A7), (B7) or (C7):
(A7)
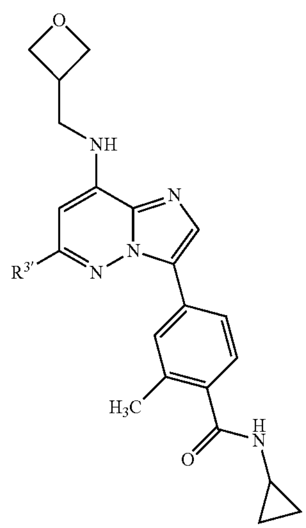
(B7)
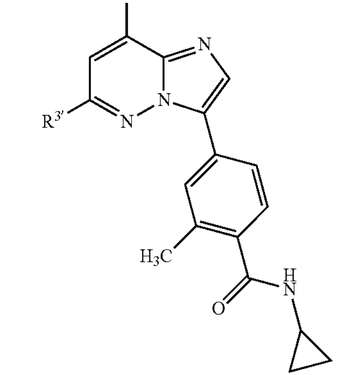

-continued
(C7)
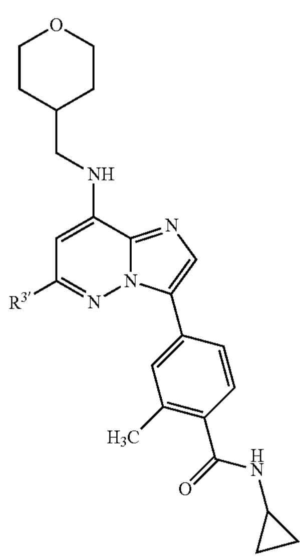
in which $R^{3'}$ is a leaving group;
with a compound of formula (A8), (B8) or (C8):
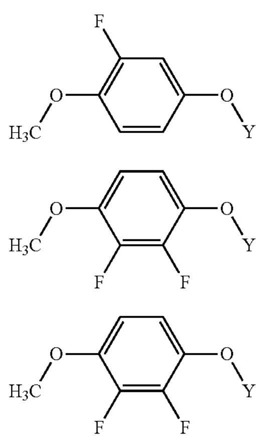
in which Y is a substituent which is displaced in a coupling reaction;
thereby giving a compound of formula (A), (B) or (C), as defined in claim 1.
9. A compound according to claim 1, which is
(B)
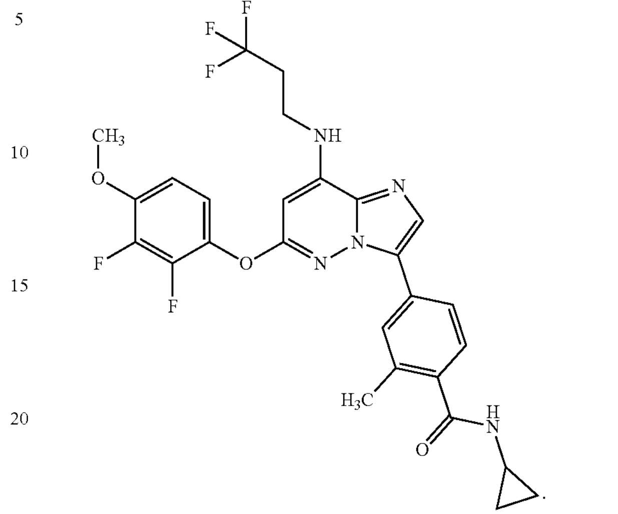
10. A compound according to claim 1, which is a salt of
(B)
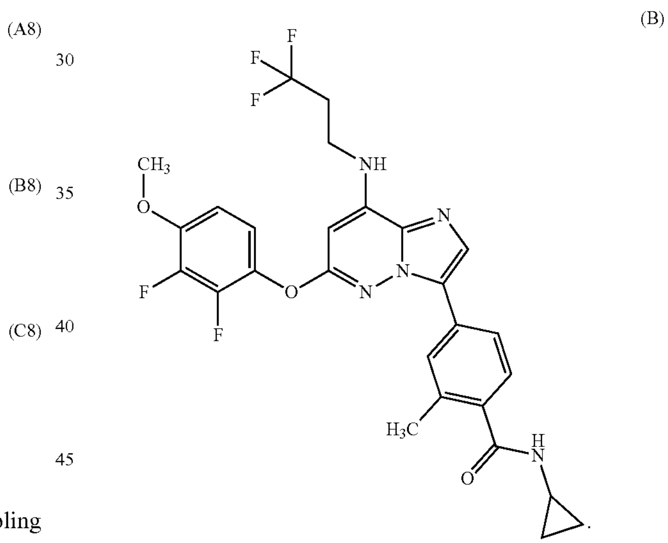
* * * * *